(12) United States Patent
Brashears et al.

(10) Patent No.: US 7,323,166 B2
(45) Date of Patent: Jan. 29, 2008

(54) LACTIC ACID BACTERIA CULTURES THAT INHIBIT FOOD-BORNE PATHOGENS

(75) Inventors: Mindy M. Brashears, Lubbock, TX (US); Divya Jaroni, York, NE (US)

(73) Assignee: Board of Regents University of Nebraska, Lincoln, NE (US)

(*) Notice: Subject to any disclaimer, the term of this patent is extended or adjusted under 35 U.S.C. 154(b) by 500 days.

(21) Appl. No.: 10/463,983

(22) Filed: Jun. 18, 2003

(65) Prior Publication Data

US 2004/0043012 A1    Mar. 4, 2004

Related U.S. Application Data

(60) Provisional application No. 60/389,968, filed on Jun. 19, 2002.

(51) Int. Cl.
*A61K 45/00*     (2006.01)
*C12N 1/20*      (2006.01)

(52) U.S. Cl. .................... 424/93.45; 435/252.3
(58) Field of Classification Search ............. 424/93.45; 435/252.3
See application file for complete search history.

(56) References Cited

U.S. PATENT DOCUMENTS

| | | |
|---|---|---|
| 3,953,609 A | 4/1976 | Farr |
| 5,186,962 A | 2/1993 | Hutkins et al. |
| 5,308,615 A | 5/1994 | DeLoach et al. |
| 5,340,577 A | 8/1994 | Nisbet et al. |
| 5,401,501 A | 3/1995 | Pratt |
| 5,478,557 A | 12/1995 | Nisbet et al. |
| 5,549,895 A | 8/1996 | Lyon et al. |
| 5,604,127 A | 2/1997 | Nisbet et al. |
| 5,807,546 A | 9/1998 | Stern et al. |
| 5,928,686 A | 7/1999 | Ivey et al. |
| 5,951,977 A | 9/1999 | Nisbet et al. |
| 5,965,128 A | 10/1999 | Doyle et al. |
| 5,985,336 A | 11/1999 | Ivey et al. |
| 6,010,695 A | 1/2000 | Line et al. |
| 6,039,984 A | 3/2000 | Bowling et al. |
| 6,110,455 A | 8/2000 | Hargis et al. |
| 6,126,961 A | 10/2000 | Kross |
| 6,203,835 B1 | 3/2001 | Westermarck et al. |
| 6,214,335 B1 | 4/2001 | Stern et al. |
| 6,228,355 B1 | 5/2001 | Byrd, II et al. |
| 2002/0192202 A1 | 12/2002 | Naidu |

FOREIGN PATENT DOCUMENTS

WO    WO 89/05849    6/1989
WO    WO 99/08532 A1    2/1999

OTHER PUBLICATIONS

Chou et al. 1999. Isolation and Characterization of Acid- and Bile-Tolerant Isolates from strains of *Lactobacillis acidophilus*, Journal of Dairy Science, vol. 82, pp. 23-31.*
Kozlova et al. 1992. English Abstract, Antibiotic Resistance of *Lactobacillus*. Antibiotiki I Khimioterapiia (Antibiotics and Chemotherapy, Russian), vol. 37, issue 6, pp. 12-15.*
Zhao, T. 1998. Reduction of Carriage of Enterohemorrhagic *Escherichia coli* O157:H7 in Cattle by Inoculation with Probiotic Bacteria. J. Clinical Microbiology, vol. 36, pp. 641-647.*
International Search Report for application No. PCT/US/03/19106, dated Nov. 3, 2003.
Meng, J. et al. "Competitive Exclusion as a Method to Prevent Colonization of *Escherichia coli* O157:H7 in Cattle", Society for Industrial Microbiology Annual Meeting, Jul. 1996, Abstract.
Amezquita et al., Competitive Inhibition of Listeria monocytogenes in ready-to-eat meat products by lactic acid bacteria, J. Food Prot., Feb. 2002; 65(2): 316-25.
Brashears et al., Antagonistic action of *Lactobacillus lactis* toward *Salmonella* spp. and *Escherichia coli* O157:H7 during growth and refrigerated storage, J. Food Prot., Nov. 1999, 62(11): 1336-1340.
Brashears et al., Isolation, selection, and characterization of lactic acid bacteria for a competitive exclusion product to reduce shedding of *Escherichia coli* O157:H7 in cattle, J. Food Prot., Mar. 2003, 66(3): 355-63.
Brashears et al., Prevalence of *Escherichia coli* O157:H7 and performance by beef feedlot cattle given *Lactobacillus* direct-fed microbials, J. Food Prot, May 2003, 66(5): 748-54.
Chou, L. and Weimer, B., Isolation and characterization of acid and bile-tolerant isolates from strains of *Lactobacillus acidophilus*, J. Dairy Sci., 1999, 82: 23-31.
Elder, R.O., Keen, J.E., Siragusa, G.R., Barkocy_Gallagher, G.A., Koohmarie, M., and Lagreid, W.W., Correlation of enterohemorrhagic *Escherichia coli* O157:H7 prevalence in feces, hides, and carcasses of beef cattle during processing, PNAS, 2000, 97: 2999-3003.
Gilliland et al., Importance of bile tolerance of *Lactobacillus acidophilus* used as a dietary adjunct, J. Dairy Sci., Dec. 1984, 67(12): 3045-3051.

* cited by examiner

*Primary Examiner*—David M. Naff
*Assistant Examiner*—Kailash C. Srivastava
(74) *Attorney, Agent, or Firm*—Suiter Swantz pc llo

(57) ABSTRACT

The present invention provides methods and compositions for preventing or inhibiting human food-borne pathogens in animals, and methods for increasing feed efficiency in animals by administering to the animal effective amounts of probiotic lactic acid producing bacteria. Further provided are feed compositions comprising probiotic lactic acid producing bacteria. A preferred probiotic lactic acid producing bacteria is *Lactobacillus acidophilus* strain ATCC accession number PTA-5249. This bacterial strain inhibits nalidixic acid-resistant *Escherichia coli* O157:H7.

6 Claims, 8 Drawing Sheets

LACTIC ACID BACTERIA CULTURES THAT INHIBIT FOOD-BORNE PATHOGENS

CROSS REFERENCE TO RELATED APPLICATION

This application claims priority from Provisional Application Ser. No. 60/389,968 filed on Jun. 19, 2002, which is hereby incorporated by reference in its entirety.

FIELD OF THE INVENTION

The invention relates to probiotic lactic acid bacteria used to prevent or inhibit the carriage of human pathogenic organisms in animals. More particularly, the invention relates to probiotic lactic acid bacteria selected for specific characteristics useful in the prevention of carriage of human pathogenic bacteria, including *E. coli* 0157:H7, in mature ruminant animals.

BACKGROUND OF THE INVENTION

Food-borne diseases are an important public health concern. In the United States alone, the occurrence of food-borne illness is estimated to be between 6 and 80 million illnesses with approximately 9000 deaths annually. The most prevalent agent causing food-borne illness is *Campylobacter jejuni*. This agent alone is estimated to be responsible for causing 4 million of these cases with more than 1000 deaths annually. Although less prevalent than *Campylobacter jejuni*, *Salmonella* (non-typhoid) is also a major health concern because it is responsible for 2 million cases of disease and approximately 2000 deaths each year. Further, more than 25,000 of these cases with more than 200 deaths annually have been attributed to food-borne *Escherichia Coli* 0157:H7. And while the incidence of disease due to *E. Coli* O157:H7 is much more rare than many other food-borne pathogens, such as *Salmonella* and *Campylobacter*, it is a particular concern because it is often life-threatening in children and the elderly.

Equally, in addition to the staggering health concerns associated with food-borne illness, is the severe economic burden these agents cause. This economic burden is not limited to one specific area of the economy, but stretches through several sectors. For example, human health costs associated with food-borne illness is estimated to be approximately 22 billion dollars annually in the United States alone. Equally devastating are the somewhat intangible costs incurred by the livestock industry, such as treatment costs and livestock deaths, negative public perception, increased cull rates, reduced feed efficiency, and decreased weight gain.

Animals have been identified as a major source of these food-borne illnesses when humans consume meat and other products contaminated with microorganisms at slaughter. In particular, the deadly food pathogen, *E. coli* O157:H7, is predominantly found in the intestinal tract of cattle. Food processors and government agencies have responded to this problem by instituting hazard analysis/critical control point (HACCP) models to provide food safety assurance. In fact, this program is required by the USDA in most meat and poultry processing facilities. HACCP systems are designed to systematically prevent food safety hazards from occurring. While HACCP has resulted in a decreased risk of contamination during the post-harvest period, it does not address the issue of contamination caused in the pre-harvest period.

Accordingly, there is growing consensus that control of food-borne pathogens in live animals is the most effective strategy for further reducing human food-borne illness. Toward that end, vaccination has been one approach employed to protect animals from carriage of microorganisms causing food-borne illness in humans. Vaccines, however, are not entirely effective in reducing the carriage of human, food-borne pathogens because many of these pathogens do not actually infect the animal, but merely reside in the animal's intestinal tract. As a result, vaccination is largely ineffective in preventing the slaughter-house contamination of meat intended for human consumption. Further diminishing the attractiveness of a vaccine based approach is the growing concern that the presence of antibiotic resistant genes in vaccines is resulting in the development of resistant populations of harmful bacteria.

Recently, the use of competitive exclusion products ("CEP"), such as probiotics, for inhibiting the carriage of food-borne pathogens in live animals has shown significant promise. Competitive exclusion employs the use of live microbial cultures that are not harmful to the animal and are also not harmful to humans. These microbial cultures are able to out compete food-borne pathogens in the animal's intestinal tract and prevent pathogens from colonizing. The use of a CEP based approach is thus promising, because unlike the vaccine based approach, CEPs are able to beneficially alter the microflora in the intestinal tract of the animal thereby reducing or eliminating the carriage of harmful human pathogens.

Probiotics, as discussed above, are an important class of CEP that have been reported to inhibit many food-borne pathogens including *Escherichia coli*, *Campylobacter jejuni*, *Salmonella*, and *Listeria monocytogenes*. Many classes of microorganisms are employed as probiotics including yeasts such as *Saccharomyces* and *Torulopsis*, fungi such as *Aspergillus*, and microorganisms belonging to the genera *Bacillus* and *Clostridium* have also been used.

Intestinal strains of lactic acid bacteria, however, are the most widely utilized class of microorganisms as probiotics. Lactic acid bacteria are widely employed as probiotics because members of this bacterial group are particularly suitable as antagonistic microorganisms in food due to their ability to inhibit other food-borne bacteria coupled with their ability to be used safely. For example, Nisbet et al. (U.S. Pat. No. 5,340,577) reported the reduction of *Salmonella* concentration in fowl using a probiotic mixture containing several lactic acid bacteria. Despite these advantages and successful use in fowl, however, lactic acid bacteria have not been employed as a means to reduce the carriage of food-borne pathogens in mature ruminant animals.

Accordingly, a need exists for a probiotic containing lactic acid bacteria effective in treating or preventing the carriage of food-borne pathogens in mature ruminant animals. The present invention addresses this need by providing strains of lactic acid bacteria that may be safely and economically employed as probiotics in mature ruminant animals.

SUMMARY OF THE INVENTION

Among the several aspects of the invention, therefore, is provided a method of preventing or inhibiting the carriage of human food-borne pathogens in mature ruminant animals by administering a probiotic lactic acid bacteria specifically selected for certain characteristics, including survivability in the gastrointestinal tract, adhesiveness to intestinal epithelium, antibiotic susceptibility, and technological properties.

Another aspect of the present invention provides a method for increasing feed efficiency in a mature ruminant by administering to the animal an effective amount of a composition comprising a probiotic bacterial strain. Further provided are feed compositions comprising the probiotic bacterial strain.

Other features of the present invention will be in part apparent to those skilled in the art and in part pointed out in the detailed description provided below.

BRIEF DESCRIPTION OF THE DRAWINGS

These and other features, aspects, and advantages of the present invention will become better understood with regard to the following description, appended claims and accompanying figures where:

ABBREVIATIONS AND DEFINITIONS

Figure 1:
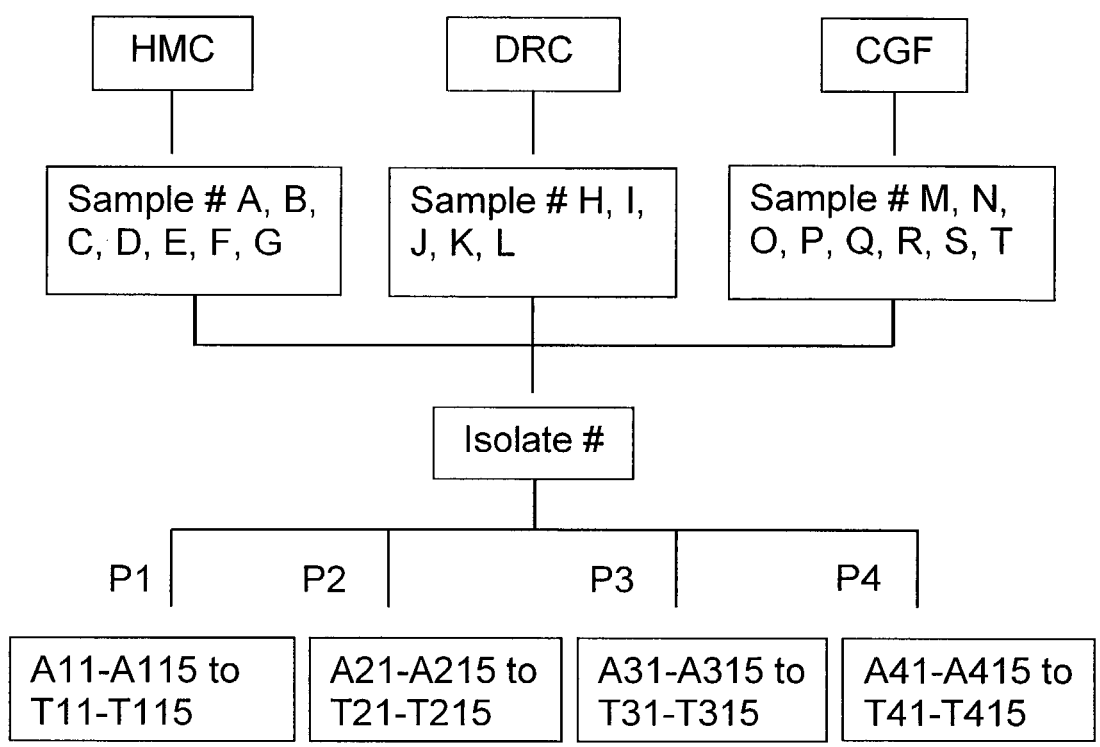
FIG. 1 depicts the nomenclature of isolates based on diets, sample collection from cattle at 3, 6, 9 and 12 weeks, and number of isolates from each sample. The letters A through T represent each animal in a diet group from which fecal samples were collected. P1 through P4 represent the time periods at which samples were collected; P1 represents the first 3-week interval, P2 represents the second 3-week interval, P3 represents the third 3-week interval, and P4 represents the fourth 3-week interval (for a total of 12 weeks). A11-T415 represent isolated colonies, with each colony collected from a given animal (A through T) at a given period of time (P1 through P4). For example, A215 represents isolate number 15 obtained during the second 3-week interval from animal A.

To facilitate understanding of the invention, a number of terms and abbreviations as used herein are defined below:

"CGF" stands for corn gluten feed.

"d" stand for days.

"DRC" stands for dry rolled corn diet.

"Enteropathogenic" shall include a microorganism capable of causing disease in the intestinal tract.

"Food-borne Pathogenic Bacteria" shall include a microorganism that is pathogenic to humans when present in food that is consumed by a human.

"HMC" stands for high moisture corn diet.

"h" stands for hour.

The term "inhibition" when used herein in phrases such as "carriage inhibition" or "inhibition of carriage" means a decrease in growth, in terms of number of target bacteria, as compared to the growth or concentration that would occur in the absence of the application of the method of the invention.

"lb" stands for pound.

"Mature Ruminant" shall include a ruminant having a stomach wherein all four compartments are functioning.

"Probiotic" shall include a mono- or mixed culture of live microorganisms which, applied to a man or animal (e.g., as dried cells or as a fermented product), affects beneficially the host by improving the properties of the indigenous microflora.

"Ruminant" shall include mature and immature animals with multi-compartment stomachs, including but not limited to, cattle, sheep, deer, goats, musk, ox, buffalo, giraffe and camels. For example, cattle and sheep have a stomach with four compartments comprising the rumen, reticulum, omasum, and abomasum.

DESCRIPTION OF THE PREFERRED EMBODIMENTS

An efficient, safe, and economical method to prevent or treat the carriage of food-borne, pathogenic bacteria in mature ruminant animals has been discovered. This method, unlike previous approaches, advantageously comprises administering to the mature ruminant an effective amount of a probiotic containing one to several strains of lactic acid bacteria ("LAB"). LAB, as previously stated, are particularly beneficial for use as a probiotic due to their ability to inhibit other food-borne bacteria coupled with their ability to be used safely in food to be consumed by humans. Several strains of LAB that are suitable for use as a probiotic to prevent or treat the carriage of food-borne, pathogenic bacteria in mature ruminant animals have been discovered.

The probiotics employed in the present invention, as stated above, generally prevent or treat the carriage of food-borne, pathogenic bacteria in ruminant animals. It is believed, without being bound by any particular theory, that the probiotics employed in the invention act by competitive exclusion ("CE"). Competitive exclusion is the use of live microbial cultures that exhibit antagonistic effects against specific groups of organisms, such as food-borne pathogens, resulting in the overall decrease in numbers of the pathogen in the intestinal tract. Although not well studied, the mechanisms by which competitive exclusion products exclude pathogens from the intestinal tract that have been observed include: (1) production of antibacterial agents (bacteriocins) and primary metabolites (organic acids and hydrogen peroxide) that may inhibit pathogenic microflora; (2) competition for nutrients; and (3) competition for adhesion sites on the gut epithelial surface that may prevent colonization by pathogenic microorganisms.

Typically the probiotic may be administered to a number of different animals. In general, however, probiotic LAB are host specific. Thus, for example, Lactobacillus isolated from a specific site of a specific animal source typically colonizes epithelium of the same kind. Generally, therefore, LAB are isolated from an animal species and administered as a probiotic to an animal from the same species. In one embodiment, LAB are isolated from mature ruminants for use as probiotics in mature ruminants. It is, however, also envisioned that LAB may be isolated from a variety of livestock animals, including but not limited to, fowl, equine, ruminants and porcine and administered as a probiotic to the particular animal species. The methods described herein enable one skilled in the art to isolate the corresponding probiotic LAB in a target animal. Equally, any known method for bacterial isolation, modified for mature ruminant animals, may be employed, such as, for instance, methods described in Buck, L. M. and S. E. Gilliland., Comparisons of freshly isolated strains of *Lactobacillus acidophilus* of human intestinal origin for ability to assimilate cholesterol during growth. J. Dairy Sci. 77: 2925, 1994.

The probiotics employed in the present invention typically comprise from one to several strains of LAB. In one embodiment, the probiotics comprise from one to ten different strains of LAB. In yet another embodiment, the probiotic comprises from two to five different strains of LAB. In still another embodiment, the probiotic comprises more than ten different strains of LAB.

In general, LAB constitute a group of Gram-positive bacteria that share similar morphologic, metabolic and physiologic characteristics. These bacteria are non-spore forming rods and cocci that ferment carbohydrates forming lactic acids as the major end-product, hence giving way to the name LAB. Depending on the metabolic pathways used to ferment carbohydrates and the resulting end products, LAB are divided into two major groups, homofermentative or heterofermentative. They are generally catalase-negative, anaerobic in nature, non-motile and do not reduce nitrate. LAB are widespread in nature with distribution common in milk and dairy products, other fermented foods, intact and rotting vegetable material, silage and intestinal tracts and mucous membranes of man and animals.

Typically, for a LAB to be a useful probiotic to prevent or treat the carriage of food-borne, pathogenic bacteria in mature ruminant animals, the bacteria are typically isolated from mature ruminant animals and are selected so that they possess certain characteristics. In the present invention, the LAB employed as a probiotic typically have the following features:

(a) Survival in the Gastrointestinal Tract

The probiotic LAB of the present invention should be able to survive and metabolize in the intestine of the mature ruminant. This means that the strain is typically resistant to gastric acid juices, low pH, enzymes, organic acids and bile and pancreatic secretions;

(b) Adhesion to Intestinal Epithelium

The probiotic LAB of the present invention should have good adhesion properties to the intestinal cells of the mature ruminant thereby enhancing colonization of the LAB. Adhesion is also desired to prevent the LAB from being washed away by contents of the stomach, intestine and by peristalsis;

(c) Antibiotic Susceptibility

It is believed that antimicrobials used in food-producing animals can promote the emergence of resistance in probiotics that can lead to transfer of resistance to other pathogenic bacteria by exchange of genetic material, or it can increase the potential threat posed by these organisms as opportunistic pathogens. In one embodiment, therefore, the LAB is not resistant to antibiotics. In another embodiment, the LAB is typically not resistant to more than 4 of the following antibiotics: erythromycin, tetracycline, ampicillin, grepafloxicin, levofloxacin, trimthoprim/sulfamethoaxozole, vancomycin, cephalothin and polymixin B. In yet another embodiment, the LAB is not resistant to more than 2 of the above-identified antibiotics. In still another embodiment, the LAB is not resistant to any of the above-identified antibiotics; and (d) Technological Properties The probiotic LAB generally undergoes several processing steps before use as a feed supplement. Such processing steps may involve, separation by centrifugation or filtration, fermentation in cultured products, and freeze-drying or lyophilization. Therefore, the LAB should be able to withstand stresses associated with these procedures such as freezing, high pressure and temperatures (60-80° C. for 5-10 minutes during pelleting) and should have a high growth rate and achievable cell mass. In addition, the LAB should be able to retain its viability under storage conditions.

LAB bacteria possessing the desired characteristics described above may be employed as a probiotic in the present invention. Typically, however, the LAB is selected from among the genera *Lactobacillus, Lactococcus, Leuconostoc, Pediococcus, Enterococcus* and *Streptococcus*. In one embodiment the LAB employed as a probiotic is from the genera *Lactobacillus*. In yet another embodiment, the strain of *Lactobacillus* is selected from *L. acidophilus, L. bulgaricus, L. helveticus, L. casei, L. lactis, L. plantarum, L. rhamnosus, L. reuteri, L. fermentum, L. brevis, L. delbreukii, L. cellobiosus*, and *L. salivarius*.

In yet another embodiment, the probiotic comprises a LAB strain isolated based upon the criteria set forth above and depicted in the examples below. This strain has been identified as *L. acidophilus* M35 (also referred to herein as M35 only)(ATCC accession no. PTA-5249).

The probiotic can be administered to the animal by a method likely to introduce the LAB into the digestive tract. In one embodiment, lyophilized LAB is thawed and mixed with the animal's feed or drinking water. Lyophilization (freeze-drying) can be performed by freezing a bacterial culture and concentrating it under vacuum to sublime the water from the frozen preparations. Briefly, cells are harvested by centrifugation, resuspended in lyophilization media and frozen at −70° C. in lyophilization vials. Vials are then placed on the lyophilizer and lyophilized for, e.g., 3 hours at e.g., Itoreq 20 millitorrs and −100° C. The vials are next sealed and stored at refrigerated or freezer temperatures until rehydration. Modifications to this protocol, depending on the cells to be lyophilized, can be easily made by one of ordinary skill in the art.

It should be noted that several factors play a role in viability and storage time of lyophilized bacteria. First, at the time of harvesting, it is preferable that the cultures are healthy and actively growing in either the logarithmic or early stationary phase, and have a density of about $10^8$/ml. It is also important that the medium for cell preservation contains a cryoprotective reagent, such as, e.g., skim milk, sucrose, serum, inositol, or dextran. However, it should also be noted that the selection of media and cryoprotective agents is an empirical process that depends on bacterial cells to be lyophilized. A skilled artisan can easily determine optimal lyophilization conditions for particular bacteria. In addition, methods for preserving cells, including the lyophilization methods are numerous and well known in the art. See, for instance, Maintenance of Microorganisms, Kirsop, B. E., and Snell, J. J. S., Eds., (1984), Academic Press, New York). Alternatively, lyophilization of bacteria is commercially available.

In another embodiment, the LAB is mixed with a carrier and applied to liquid or solid feed or to drinking water. The carrier material should be non-toxic to both the LAB and the animal. The carrier will generally contain an ingredient that promotes viability of the LAB during storage. When administered in feed or drinking water the dosage can be spread over a period of days or even weeks. In yet another embodiment, the LAB is formulated as an inoculant paste to be directly injected into an animal's mouth. The formulation can include additional ingredients to improve palatability, improve shelf-life, impart nutritional benefits, and the like. In still a further embodiment, if a reproducible and measured dose is desired, the LAB can be administered by rumen cannula.

The effective amount of probiotic administered to the animal is a quantity to achieve the desired carriage inhibition of food-borne, pathogenic bacteria. This effective amount can vary depending on many factors, such as, the size of the animal, the species of the animal, the age of the animal, the particular active compound used, the dosage form employed or the particular sensitivity of the particular animal. The optimum range of an effective amount, based on variables such as those mentioned above, can be found using conventionally known techniques, for example, such as, dose titration determinations or any other method generally known in the veterinary sciences. For example, by monitoring the numbers of target pathogen in the feces before, during and after administration of probiotic, the skilled artisan can readily ascertain the dosage level.

In one embodiment, the probiotic is administered as a preventative, to prevent animals not presently carrying the pathogen from acquiring the strain by exposure to other animals or environments where the pathogen is present. In yet another embodiment, the probiotic is administered to treat animals carrying a pathogen. For example, animals known to be shedding a pathogen in feces, or those raised where a pathogen is known to exist are suitable candidates for treatment with probiotic. The methods for administering probiotic are essentially the same, whether for prevention or treatment.

The probiotic LAB of the present invention may be administered to a mature ruminant to prevent or treat the carriage of a number of target food-borne, pathogenic bacteria for which the probiotic is effective against. In general, the term "food-borne, pathogenic bacteria" means that the bacteria is pathogenic to humans. Depending on the particular strain of LAB utilized, however, the probiotic may also be effective against bacteria that are pathogenic to the host animal, such as mature ruminant animals. In one embodiment, the target food-borne, pathogenic bacteria is a strain of human enteropathogenic bacteria. In yet another embodiment, the human enteropathogenic bacteria is selected from *Campylobacter jejuni, Salmonella, Escherichia coli, Listeria monocytogenes*, and *Vibrio*. In still another embodiment, the target bacteria is *Escherichia coli*. In yet another embodiment, the target bacteria is *E. coli* O157:H7.

EXAMPLES

It is understood that the foregoing examples are given by way of illustration and that modifications and variations may be made therein without departing from the spirit and scope of the invention.

Example 1

Isolation of Strains of LAB From Healthy Cattle

Cattle that were fecal culture negative for *E. coli* O157:H7 were selected to supply fecal samples for isolation of LAB that were to be screened for inhibitory activity towards *E. coli* O157:H7. Manure sample from the Animal Science Department of University of Nebraska-Lincoln (UNL) were obtained at three-week intervals over a period of twelve weeks (4 sampling periods) from cattle that were fed three different finishing diets, (1) High Moisture Corn (HMC), (2) Dry Rolled Corn (DRC), and (3) Corn Gluten Feed (CGF) (Table 1). Samples were collected separately from 5-7 cows from each diet group and numbered as illustrated in FIG. 1.

One gram of each fecal sample was added to 10 ml of sterile de Man-Rogosa-Sharpe (MRS) broth (Difco Becton Dickinson Microbiology Systems, Sparks, Md.) and mixed thoroughly by shaking. The fecal material was then plated on Lactobacillus Selection (LBS) agar (BBL Becton Dickinson Microbiology Systems, Cockeysville, Md.) and MRS agar plates using the streak-plate method. The plates were incubated at 37° C. for 48 hours in plastic bags flushed with $CO_2$ for 30 seconds. Approximately 10 to 15 well-isolated colonies were picked from each plate and transferred to individual tubes containing 10 ml of MRS broth, which were further incubated at 37° C. for 18-72 hours to obtain maximum growth of the cultures. The isolated cultures were restreaked onto LBS and MRS agar plates and incubated at 37° C. for 48 hours. This process was repeated until only one colony morphology appeared. Following isolation, pure colonies were Gram-stained according to the Bergey's Manual of Determinative Bacteriology (Sneath P. H. A., N. S. Mair, M. E. Sharpe, and J. G. Holt (ed.), Bergey's Manual of Systematic Bacteriology, Williams and Wilkins, MD.) for preliminary identification. The isolated cultures were maintained as frozen (−70° C.) stocks in MRS broth supplemented with 10% (v/v) sterile glycerol. Isolates were subcultured in MRS broth at 37° C. for 24-48 hours before they were used for further studies.

TABLE 1

Composition of diets fed to cattle utilized for isolation of bacteria

| Ingredient[a] | HMC | DRC | CGF |
|---|---|---|---|
| Alfalfa | 7.5% | 75.5% | 7.5% |
| Molasses | 3.0% | 3.0% | — |
| Supplemental[b] | 5.0% | 5.0% | 5.0% |
| HMC | 84.5% | — | — |
| DRC | — | 84.5% | 47.5% |
| CGF | — | — | 40.0% |

HMC - High Moisture Corn; DRC - Dry Rolled Corn; CGF - Corn Gluten Feed
[a]Dry matter basis
[b]Protein mineral and vitamins Six hundred eighty-six isolates were obtained; 15% were Gram-negative and 85% were Gram-positive bacteria with 72% Gram-positive rods and 27% Gram-positive cocci, as determined by the Gram-staining procedures followed by microscopic examination. Isolates were obtained from all animals on all diets.

Example 2

Screening Isolated Colonies for Inhibition Towards *E. coli* O157:H7

Isolated strains were initially screened for inhibition towards *E. coli* O157:H7 using the agar spot test. An overnight culture of each cattle isolate to be tested was prepared by inoculating stock culture in 10 ml of MRS broth. Cultures of individual strains were then spot-inoculated onto the surface of MRS agar plates and incubated for 24-48 hours at 37° C. in plastic bags flushed with $CO_2$ for 30 seconds. A four-strain mixture of *E. coli* O157:H7 was used to screen the isolates for inhibitory activity towards *E. coli* O157:H7. The *E. coli* strains used in the study were originally obtained from the laboratory of Charles Kaspar (Food Research Institute, University of Wisconsin, Madison, Wis.) and included strains 920, 922, 944, and 966 (all cattle isolates). Overnight cultures of *E. coli* strains were prepared ($5 \times 10^8$ CFU/ml) by inoculating 10 ml of tryptic soy broth (TSB) (Difco Becton Dickinson Microbiology Systems, Sparks, Md.) with frozen (−70° C.) stocks of each *E. coli* strain and incubating at 37° C. for 18-24 hours.

Bacterial numbers were determined by pour-plating each overnight culture on tryptic soy agar (TSA) (Difco), using appropriate dilutions, and incubating at 37° C. for 18 hours. The cocktail of *E. coli* O157:H7 was prepared by placing 1 ml of the overnight culture of each strain into a sterile test-tube and thoroughly mixing. About 1 ml of the cocktail mixture was inoculated into 10 ml of tempered soft TSA to obtain a final concentration of approximately $5 \times 10^7$ CFU/ml. This mixture was then poured onto the surface of spot-inoculated agar plates that contained well-grown test isolates. After 24 hours of incubation at 37° C., inhibitory activity of the test isolate was measured as the size of inhibition zones around the colony. Inhibition was considered significant when the width of the clear zone around the colonies of the isolated strains was 0.5 mm or larger. The test for each isolate against the pathogen cocktail was replicated three times.

Figure 2:
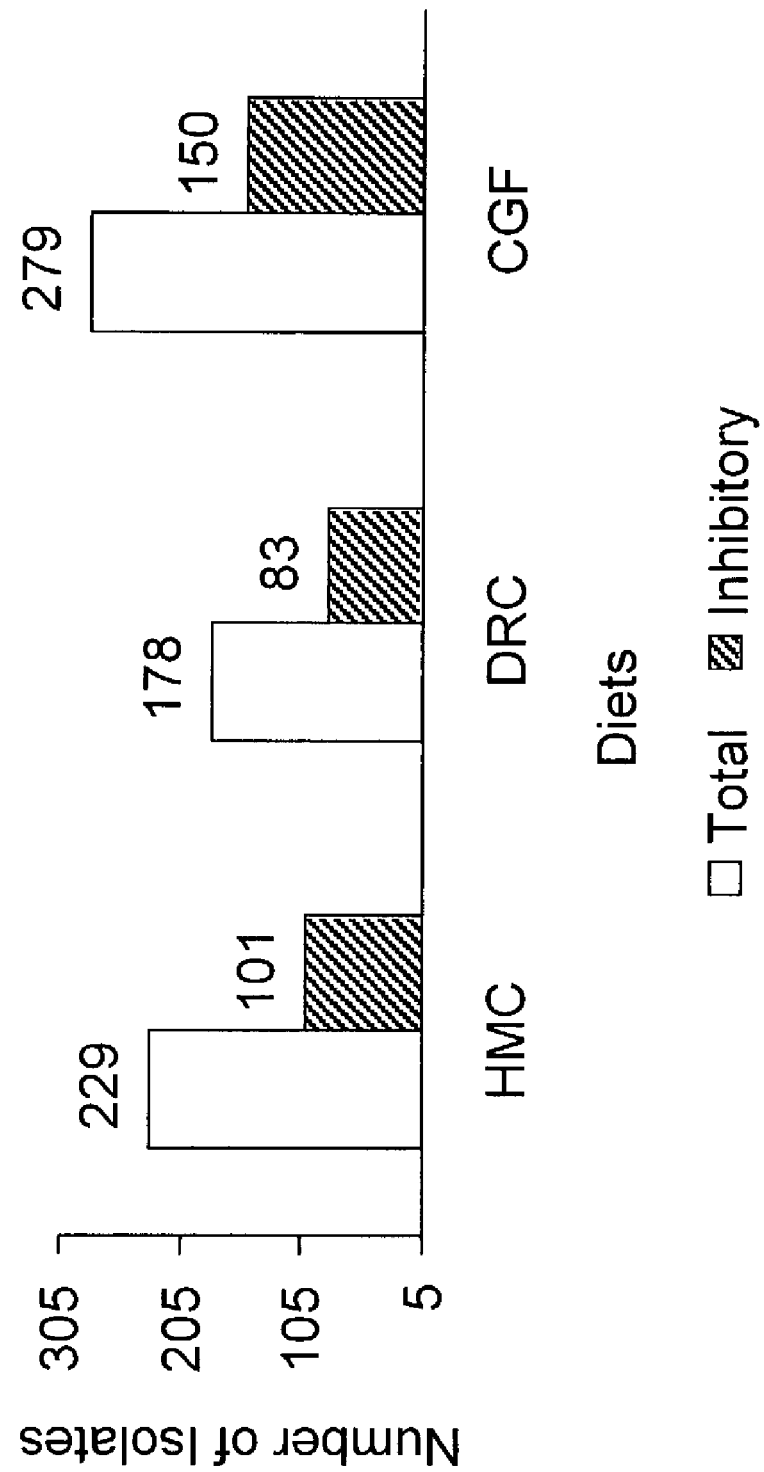
FIG. 2 is a graphic representation of inhibition of *E. coli* O157:H7 using the agar spot test, as further described in Example 2, by strains isolated from cattle fed 3 different diets: corn gluten feed diet, dry rolled corn diet, high moisture corn diet.

All 686 isolates were tested for inhibition towards *E. coli* O157:H7 using agar spot test. Three hundred fifty-five isolates (52%) met or exceeded the inhibition criteria (inhibition zone ≧0.5 mm) and 275 isolates (40%) produced inhibition zones near or greater than 1 mm. The inhibition zones ranged from 0.5 mm to as large as 12 mm. Results are shown in FIG. 2. In addition, for specific values of a number of isolates, see Table 3 (inhibition column).

Example 3

Test for Bile Tolerance

The isolates that were most inhibitory towards *E. coli* O157:H7 in the agar spot test were selected for bile tolerance tests. The method used for testing bile tolerance was similar to the one described by Gilliland et al. (Gilliland, S. E., Stanley, T. E., and Bush, L. J. 1984. Importance of bile tolerance of *Lactobacillus acidophilus* used as a dietary adjunct. J. Dairy Sci. 67: 3045-3051). An overnight culture of the selected isolates was prepared in 10 ml MRS broth and 0.1 ml of the culture suspension was inoculated into tubes containing 10 ml MRS broth with 0.5, 0.15, 0.3% oxgall or without oxgall (control). The inoculated tubes were incubated at 37° C. in a water bath. Growth of the organisms was monitored at 0, 2, 4, 6, and 24 hours by measuring absorbance at 660 nm. The test for each strain was repeated three times.

Bile tolerance studies indicated that all isolates except A22 showed increased growth rate under all bile conditions (0. 0.5, 0.15, and 0.30%). However, when compared with other treatments, the growth was slightly decreased for treatment containing 0.3% oxgall but showed a gradual increase over a 24 hour period with the following exceptions: (i) strains C111 and M38 showed reduced growth for 0.3% oxgall at 24 hours, and (ii) strains F111, T28, Q311, and J49 did not grow well at 0.3% oxgall at all incubation periods.

Example 4

Storage Stability

Nineteen of the 75 isolates selected for further studies were tested for storage stability in a commercial freezer (0° C.). Following isolation, an overnight culture of each isolate was prepared in MRS broth and supplemented with 10% (v/v) sterile glycerol. About 1 ml of each culture was then dispensed into sterile 1.5 ml cryogenic vials and frozen at −70° C. These frozen stocks were transferred the next day to a freezer set at 0° C. Viability of the isolates was tested at 0, and after 3 months of storage in the commercial freezer by plating on MRS agar and incubating at 37° C. for 18-24 hours.

At the end of all the screening procedures (24 months), the isolates finally selected as competitive exclusion products (CEP) were tested for viability by plating concentrated cultures on MRS agar (at appropriate dilutions) and incubating at 37° C. for 18-24 hours. Colonies were counted after incubation to determine the actual population.

All isolates maintained their viability over a period of 3 months of storage at 0° C. with the exception of isolates A43 and A46 that did not survive storage in a commercial freezer. Isolates M35 (ATCC accession no. PTA-5249) and L411 that were selected as CEP showed good survival after 24 months of storage at −70° C. A population of about $1 \times 10^9$ CFU/ml was obtained for both the isolates after culturing on MRS agar.

Example 5

Preliminary Identification of Isolates Using Analytical Profile Index (API)

Based on their inhibitory activity towards *E. coli* O157: H7, and tolerance to acid and bile, 75 isolates were chosen for identification by fermentation patterns using standard API (bioMérieux, Inc., Hazelwood, Mo.) tests. API 50CHL, API 20Strep, and API 20E were used to identify Gram-positive rods, Gram-positive cocci and Gram-negative rods, respectively.

Based on the API, some of the isolates were eliminated because either their identification was not clear (unacceptable or doubtful profile) or they were not LAB. The most commonly identified strains of LAB according to API were: *Lactobacillus acidophilus, L. fermentum, L. delbreukii, L. salivarius, L. brevis, L. cellobiosus, Leuconostoc* spp., and *Pediococcus acidilactici* (Table 2). Of the 75 isolates identified and screened for bile tolerance, 19 were selected for further interaction studies in the manure and rumen fluid. A list of the selected isolates along with their API profiles is given in Table 3.

TABLE 2

Identification of cattle isolates by Analytical Profile Index

| Cattle Isolate | API Used | Identification[a] | % Homology |
|---|---|---|---|
| M17 | 50 CHL | L. fermentum | 91.5 |
| K110 | 50 CHL | L. brevis | 99.7 |
| H27 | 50 CHL | L. delvreukii ss. delb. | 88.5 |
| I212 | 50 CHL | L. salivarius | 99.9 |
| S21 | 50 CHL | L. brevis | 99.5 |
| T28 | 50 CHL | L. acidophilus | 82.5 |
| C314 | 50 CHL | L. acidophilus | 88.3 |
| I33 | 50 CHL | L. brevis | 99.5 |
| M35 | 50 CHL | L. acidophilus | 98.5 |
| O37 | 50 CHL | L. cellobiosus | 97.2 |
| B41 | 50 CHL | L. fermentum | 98.9 |
| L411 | 50 CHL | L. acidophilus | 84.2 |
| T21[a] | 20 strep | Leuconostoc spp. | 98.3 |
| P32 | 50 CHL | L. brevis | 99.4 |
| A43 | 50 CHL | L. acidophilus | 87.5 |
| A46 | 50 CHL | L. acidophilus | 99.2 |
| C315 | 50 CHL | Pediococi acidilactici | 99.8 |
| M38 | 50 CHL | L. acidophilus | 95.8 |
| S310 | 50 CHL | L. acidophilus | 60.3 |
| R44 | 50 CHL | L. acidophilus | 95.8 |

[a]Identification to genus level only

TABLE 3

Cattle isolates chosen for further analysis based on inhibition[a] towards E. coli O157:H7, Gram reaction, bile tolerance[b] and Analytical Profile Index

| Isolate | Inhibition (mm) | Gram Rxn. | API |
|---|---|---|---|
| C315 | 11.47 | Cocci+ | Pediococcus acidilactici |
| A46 | 8.87 | Rods+ | L. acidophilus |
| C314 | 8.13 | Rods+ | L. acidophilus |
| M35 | 6.00 | Rods+ | L. acidophilus |
| M38 | 4.33 | Rods+ | L. acidophilus |
| S310 | 4.20 | Rods+ | L. acidophilus |
| B41 | 3.45 | Rods+ | L. fermentum |
| R44 | 3.15 | Rods+ | L. acidophilus |
| I212 | 2.89 | Rods+ | L. salivarius |
| O37 | 2.78 | Rods+ | L. cellobiosus |
| L411 | 2.03 | Rods+ | L. acidophilus |
| H27 | 1.71 | Rods+ | L. delbreukii. delbreukii |
| A43 | 1.65 | Rods+ | L. acidophilus |
| P31 | 1.45 | Rods+ | L. acidophilus |
| C312 | 1.39 | Rods+ | L. acidophilus |
| T21 | 1.07 | Cocci+ | Leuconstoc spp. |
| T28 | 1.03 | Rods+ | L. acidophilus |
| I33 | 1.01 | Rods+ | L. brevis |
| P32 | .97 | Rods+ | L. brevis |

[a]Agar Spot Test: Inhibition measured as the size of clear zone (in mm) around the colony
[b]Bile tolerance not shown. All isolates were resistant to all bile conditions.

Example 6

Test for Antibiotic Resistance

The isolates selected after API results were further screened for resistance to a panel of 6 antibiotics representing two of the three categories of antimicrobial drugs suggested by FDA, that are commonly used in animals and humans. The following are examples of types of drugs that would be included in the three categories: Category I: quinolones, vancomycin, dalfopristin/quinupristin, third generation cephalosporins; Category II: ampicillin, first and second generation cephalosporins, erythromycin, trimethoprim/sulfamethoxazole; and Category III: inophores (monensin) and polymixins (Polymixin B and colistin). The antibiotics used in the present study included erythromycin (EM), ampicillin (AM), tetracycline (TC), trimethoprim/sulfamethoxazole (TS), grepafloxacin (GP) (quinolone), and levofloxacin (LE) (fluoroquinolone). A commercial antimicrobial susceptibility test kit-Etest (AB Biodisk, North America Inc., Piscataway, N.J.) was used to determine the minimum inhibitory concentrations (MIC) of the antibiotics for the isolates selected. Etest strips containing a predefined exponential gradient of a particular antibiotic were applied to agar plates containing Mueller Hinton Agar (Difco) pre-inoculated with an overnight culture of the given bacteria (inoculum of 0.5 McFarland turbidity in 0.85% NaCl). The agar plates with the strips were immediately incubated at 37° C. for 16-20 hours, when bacterial growth became distinctly visible. After incubation, MIC values (μg/ml) were read where the inhibition ellipse (centered along the strip) intersected the scale at the edge of the strip. The susceptibility categorization of organisms towards a specific antibiotic was provided in the Etest antibiotic supplements for each agent and was used to examine the susceptibility of lactic acid bacteria (LAB) isolates. Based on the categorization, MIC for a particular organism was reported as susceptible (S), intermediate (I), or resistant (R). The susceptibility categories of each antibiotic are given in Table 4. When growth occurred along the entire strip, i.e. no inhibition ellipse was seen, the MIC was reported as greater than (>H) the highest value on the reading scale. When the inhibition ellipse was below the strip, i.e. the zone edge did not intersect the strip, MIC was reported as less than (<L) the lowest value on the reading scale.

Of the 19 strains tested, 21% (4 of 19) (M35 (ATCC accession no. PTA-5249), A43, C312, and I212) showed susceptibility to all the antibiotics. Most isolates were resistant to trimethoprim/sulfamethaxozole and grepafloxacin (63% and 58% respectively). Thirteen of 19 isolates (68%) showed multiple resistance (≧2) patterns most commonly to trimethoprim/sulfamethoxazole, grepafloxacin, and tetracycline. Only one isolate (B41) was resistant to levofloxacin and two isolates (T28 and C314) were resistant to ampicillin. Results are shown in Tables 4 and 5.

TABLE 4

Minimum inhibitory concentrations (g/m l) of antibiotics[a] for cattle isolates

| Isolates | EM | TS | GP | AM | LE | TC |
|---|---|---|---|---|---|---|
| I33 | 3.00 (I) | 0.44 (S) | 1.2 (I) | 0.03 (S) | 2.3 (I) | 56.0 (R) |
| O37 | 0.14 (S) | >H (R) | 9.0 (R) | 0.75 (S) | 3.0 (I) | 2.5 (S) |

TABLE 4-continued

Minimum inhibitory concentrations
(g/m l) of antibiotics$^a$ for cattle isolates

| Isolates | EM | | TS | | GP | | AM | | LE | | TC | |
|---|---|---|---|---|---|---|---|---|---|---|---|---|
| T21 | >H | (R) | >H | (R) | 12.0 | (R) | 0.87 | (S) | 2.5 | (I) | >H | (R) |
| L411 | 0.16 | (S) | >H | (R) | 6.0 | (R) | 0.87 | (S) | 2.0 | (S) | 1.75 | (S) |
| H27 | >H | (R) | >H | (R) | 12.0 | (R) | 1.12 | (S) | 2.0 | (S) | 32.7 | (S) |
| A46 | 0.11 | (S) | >H | (R) | 7.5 | (R) | 0.87 | (S) | 1.5 | (S) | 1.2 | (S) |
| T28 | <L | (S) | 1.50 | (S) | 0.10 | (S) | 48.0 | (R) | 0.1 | (S) | 1.5 | (S) |
| M35 | <L | (S) | <L | (S) | <L | (S) | 0.50 | (S) | <L | (S) | <L | (S) |
| M38 | 0.11 | (S) | >H | (R) | 7.0 | (R) | 0.87 | (S) | 2.0 | (S) | 2.0 | (S) |
| A43 | <L | (S) | <L | (S) | <L | (S) | <L | (S) | <L | (S) | <L | (S) |
| P31 | 0.11 | (S) | >H | (R) | 8.0 | (R) | 0.09 | (S) | 3.0 | (I) | 2.0 | (S) |
| C314 | >H | (R) | 6.19 | (R) | 6.25 | (R) | >H | (R) | 2.3 | (I) | 30 | (R) |
| B41 | 0.24 | (S) | >H | (R) | 1.0 | (S) | 0.56 | (S) | 17.5 | (R) | >H | (R) |
| P32 | 8.00 | (R) | 0.2 | (S) | 2.25 | (I) | 0.11 | (S) | 3.0 | (I) | >H | (R) |
| C312 | <L | (S) | <L | (S) | <L | (S) | <L | (S) | <L | (S) | <L | (S) |
| C315 | 0.22 | (S) | >H | (R) | 7.0 | (R) | 1.13 | (S) | 2.25 | (I) | 1.9 | (S) |
| I212 | 0.06 | (S) | 0.75 | (S) | 0.56 | (S) | 0.02 | (S) | 0.62 | (S) | 0.2 | (S) |
| S310 | 0.22 | (S) | >H | (R) | 6.0 | (R) | 0.75 | (S) | 2.0 | (S) | 1.5 | (S) |
| R44 | 0.13 | (S) | >H | (R) | 4.5 | (R) | 0.75 | (S) | 1.5 | (S) | 1.3 | (S) |

$^a$EM = Erythromycin; TS = Trimethoprim/Sulfamthoxazole; GP = Grepafloxacin; AM = Ampicillin; LE = Levofloxacin; TC = Tetracycline; H = Highest MIC value on the scale; 256 g/ml for EM, AM, TC and 32 g/ml for TS, GP, LE; L = Lowest MIC value on the scale Susceptibility Categorization of Antibiotics (MIC in g/m l):

| | Susceptible (S) | Intermediate (I) | Resistant (R) |
|---|---|---|---|
| EM | 4 | 8 | 16 |
| TS | 0.5 | 1-4 | 8 |
| GP | 2 | 4 | 8 |
| AM | 8 | 16 | 32 |
| LE | 1 | 2 | 4 |
| TC | 2 | — | 4 |

TABLE 5

Test of antibiotic resistance in
cattle isolates towards various antibiotics

| Antibiotic$^a$ | % Susceptible | % Intermediate | % Resistant |
|---|---|---|---|
| EM | 74.0 | 5.0 | 21.0 |
| AM | 90.0 | 0.0 | 10.0 |
| TC | 69.0 | 0.0 | 31.0 |
| TS | 37.0 | 5.0 | 63.0 |
| GP | 32.0 | 10.0 | 58.0 |
| LE | 58.0 | 37.0 | 5.0 |

$^a$EM - Erythromycin; AM - Ampicillin; TC - Tetracycline; TS - Trimethoprim/Sulphamethoxazole; GP - Grepafloxacin; LE - Levofloxacin Example 7

Test for Inhibition Against E. coli O157:H7 in Rumen Fluid and Manure

Nineteen isolates, selected from the previous screening methods, were further tested for their antagonistic action against strains of E. coli O157:H7 that were resistant to nalidixic acid. E. coli O157:H7 strains were selected for nalidixic acid-resistance to facilitate their recovery on the media during the interaction studies and to prevent background microflora from manure and rumen.

(1) Selection of Nalidixic Acid-resistant Strains of E. coli O157:H7:

The E. coli O157:H7 strains that were used in the initial inhibition study using agar spot test were selected for nalidixic acid-resistance. MacConkey Sorbitol agar (MSA) (Difco) was prepared supplemented with the following concentrations of nalidixic acid (ICN Biomedicals Inc., Aurora, Ohio: 0.1, 0.2, 0.4, 0.8, 1.6, 3.2, 6.4, 12.0, 8.0, 25, and 50 µg/ml). About 0.1 ml of a well-grown overnight culture of each E. coli O157:H7 strain was placed into separate petri dishes and overlaid with MSA containing 0.1 µg/ml of nalidixic acid. The plates were incubated at 37° C. for 18 hours. About 3-5 well-isolated colonies were then transferred to TBS, supplemented with 0.1 µg/ml nalidixic acid, and incubated further at 37° C. for 18 hours. The cells grown in TSB with 0.1 µg/ml nalidixic acid were then overlaid with MSA containing 0.2 µg/ml of nalidixic acid. The entire process was repeated with increasing concentrations of nalidixic acid in the media each time until cells were selected that were resistant to 50 µg/ml of nalidixic acid.

(2) Antagonistic Action of Cattle Isolates Against E. coli O157:H7 in Manure:

A fresh overnight culture of each selected cattle isolate was prepared in 10 ml of MRS broth. Freshly prepared culture of each of the four strains of nalidixic acid-resistant E. coli O157:H7 was inoculated into 10 ml of TSB and incubated for 18 hours at 37° C. A cocktail was prepared from all four strains by mixing them together. Manure sample of cattle was obtained from the Animal Science Department, UNL, on the day of the experiment and about 20 g was reserved for uninoculated control. The uninoculated control was used to make sure that no bacteria (that may be resistant to nalidixic acid) other than the E. coli O157:H7 strains added to the samples were being recovered on MSA supplemented with nalidixic acid. About 400 grams of manure sample was inoculated with 0.4 ml of E. coli O157:H7 cocktail to obtain a population of 1×10$^5$ CFU/ml which was divided into 20 sterile whirl pack bags (20 g each). Keeping one manure sample for inoculated control, each of the other samples was inoculated with 2 ml (1 X 10$^7$ CFU/ml) of the fresh MRS broth cultures of LAB (1 isolate/manure sample). Each of the samples thus obtained were incubated at 37° C. and plated in duplicates on MSA supplemented with nalidixic acid (50 μg/ml) at 0, 24 and 48 hours to monitor *E. coli* O157:H7 growth. The pH of each manure sample was recorded at 0, 24, and 48 hours. The entire experiment was repeated three times.

(3) Antagonistic Action of Cattle Isolates Against *E. coli* O157:H7 in Rumen Fluid:

To simulate rumen conditions, as per the method used by de Vaux et al., Displacement of *Escherichia coli* O157:H7 from rumen medium by prebiotic sugars. Appl. Environ. Microbiol. (in press), fresh bovine rumen fluid obtained from the Animal Science Dept., UNL, was mixed with 1 g/L corn starch, 2 g/L maltose and equal parts of phosphate buffer solution (272 ml of 0.2M $Na_2HPO_4$ (Fischer Scientific) and 128 ml of 0.2M $NaH_2PO_4$ (Fischer Scientific) mixed together). The mixture was sterilized and put in an anaerobic jar to facilitate thorough reduction for 1-4 days. After reduction, about 10 ml of rumen fluid mixture was reserved as uninoculated with 0.25 ml of *E. coli* O157:H7 cocktail as prepared in the manure experiment. The inoculated mixture was divided into 20 sterile tubes (10 ml each) and keeping one sample for inoculated control, the other samples were inoculated with 1 ml of freshly prepared cultures of selected LAB (1 isolate per sample). Each of the samples were anaerobically incubated at 37° C. and plated in duplicate on MSA supplemented with nalidixic acid at 0, 24 and 48 hours to monitor *E. coli* O157:H7 growth. The pH of all rumen-fluid samples was recorded at 0, 24 and 48 hours. The entire experiment was repeated three times.

The interaction of *E. coli* O157:H7 with the selected LAB was studied in the manure and rumen fluid at 0, 24 and 48 hours. As expected, none of the strains were different from the control in their inhibition against *E. coli* O157:H7 at 0 hours in both rumen fluid and manure.

Figure 3:
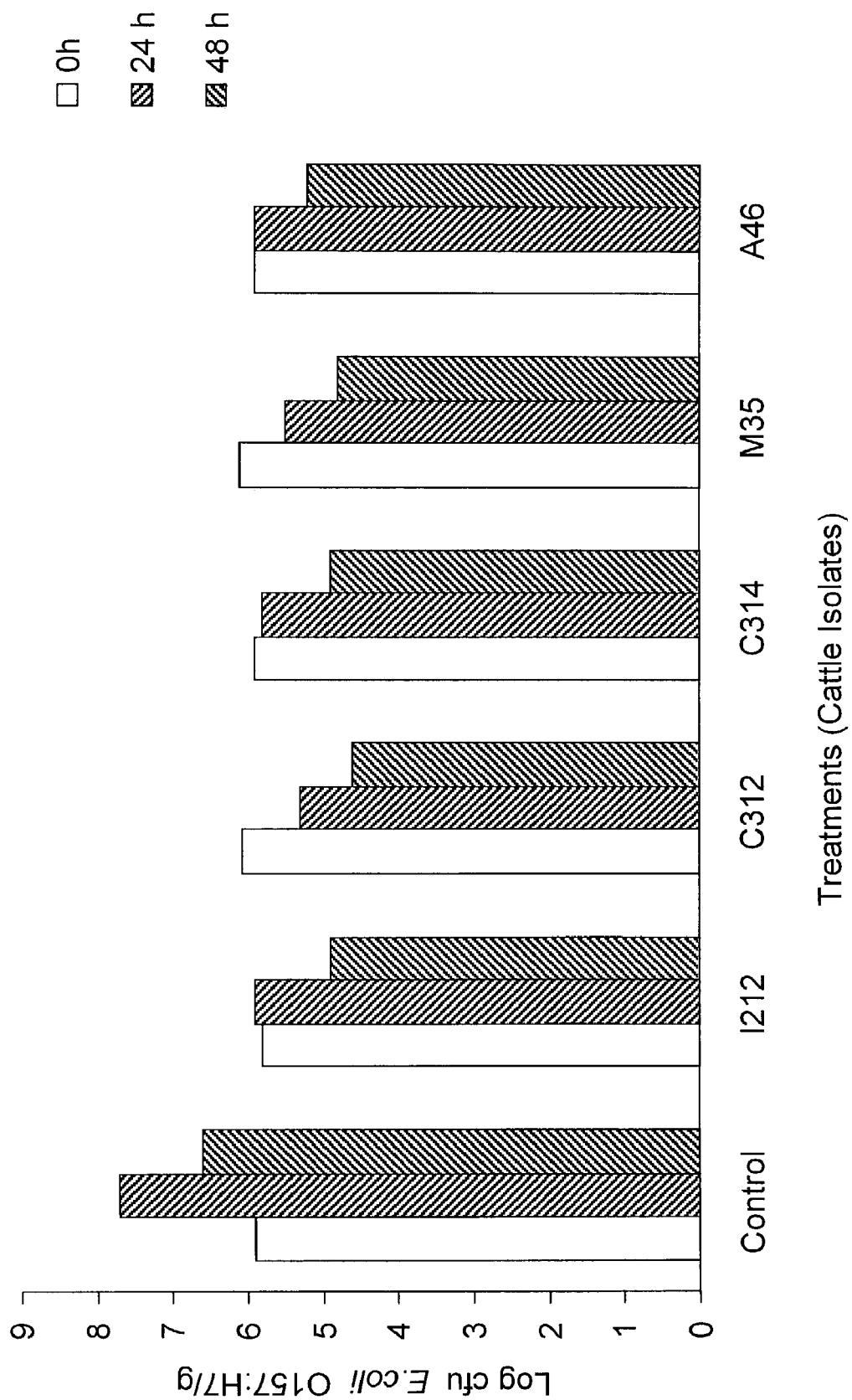
FIG. 3 is a graphic representation of inhibition of *E. coli* O157:H7 by several different lactic acid bacteria strains in manure. These strains and the interaction test are described in more depth in example 7 and in the examples accompanying tables. The control sample contained only the *E. coli* O157:H7 strain. Bars with different letters are significantly (P<0.05) different.

Results from the interaction studies in manure showed that at 24 hours, control (no LAB added) showed an increase in *E. coli* O157:H7 counts by approximately 2.0 $log_{10}$ cycles from 5.9 to 7.6 $log_{10}$ CFU/ml (Table 6 and FIG. 3). All strains except H27, T21, I33, O37, P31, P32 and B41 significantly (P<0.05) reduced *E. coli* counts (approximately 1 $log_{10}$ reduction) compared to control at 24 hours. However, at 48 hours, only strains I212, C312, C314, C315, M35 (ATCC accession no. PTA-5249), A46 and L411 were able to maintain the reduction in *E. coli* O157:H7 counts and the difference was statistically significant (P<0.05) when compared to the control. These strains were able to reduce *E. coli* O157:H7 numbers from approximately 6.0 $log_{10}$ CFU/ml to 4.6 $log_{10}$ CFU/ml over a 48 hour period. No change in pH of the treatment samples was observed at 0, 24 or 48 hours, as it ranged between 6.1-6.8 at all incubation periods.

Figure 4:
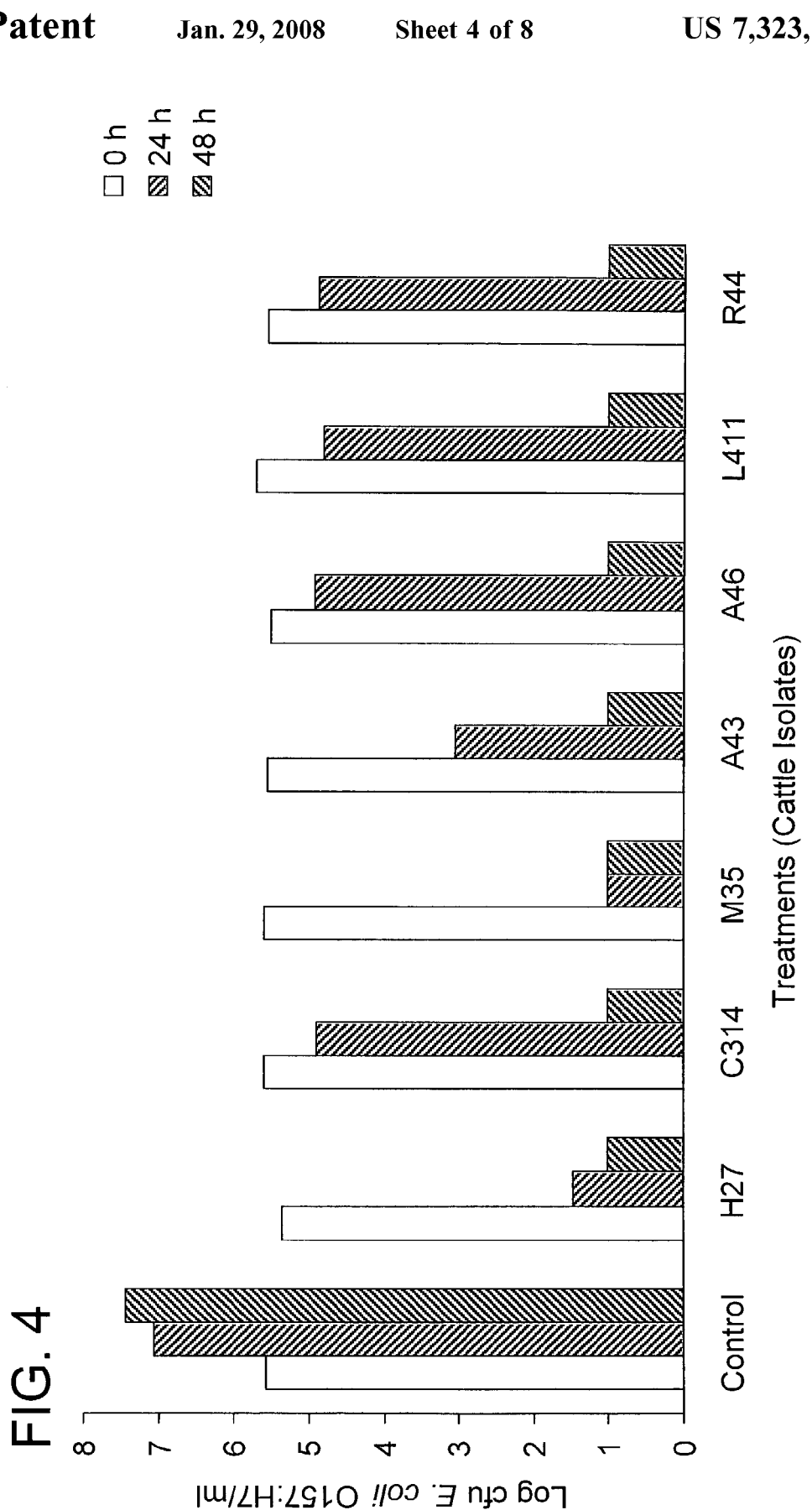
FIG. 4 is a graphic representation of inhibition of *E. coli* O157:H7 by lactic acid bacteria in rumen fluid. These strains and the interaction test are described in more depth in example 7 and in the examples accompanying tables. The control sample contained only the *E. coli* O157:H7 strain. Bars with different letters are significantly (P<0.05) different.

Interaction studies in rumen fluid revealed that at 24 hours, strains H27, T21, T28, C314, M35 (ATCC accession no. PTA-5249), M38, A43, A46, L411 and R44 significantly (P<0.05) reduced *E. coli* counts (between 1 to 4 $log_{10}$ reductions) compared to the control (see Table 7 and FIG. 4). Strain M35 (ATCC accession no. PTA-5249) completely eliminated *E. coli* O157:H7 at 24 hours by reducing the numbers from 5.6 $log_{10}$ CFU/ml to 1.0 $log_{10}$ CFU/ml. At 48 hours all of the strains except I212, C312, C315, O37, P32 and B41 significantly inhibited *E. coli* O157:H7 compared to the control (P<0.05). Strains H27, C314, M35 (ATCC accession no. PTA-5249), M38, A43, A46, L411, and R44 eliminated *E. coli* in rumen fluid at 48 h (reduction from 5.5 $log_{10}$ CFU/ml to 1.0 $log_{10}$ CFU/ml). No change in pH was observed for any of the treatments, with pH values ranging between 6.0-6.3.

In order to be able to select final strains for the CEP, isolates were also compared against each other for inhibition towards *E. coli* O157:H7. None of the strains were different from each other in their inhibition against *E. coli* in manure. However, in the rumen fluid it was found that at 24 hours, strains H27, M35 (ATCC accession no. PTA-5249) and A43 were most inhibitory towards *E. coli* O157:H7 compared to the other strains whereas at 48 hours, strains C314, M38, A46, L411 and R44 along with the aforementioned strains also showed significant reduction in *E. coli* counts when compared to the rest of the strains (P≤0.05). Uninoculated manure samples were also plated at each incubation period to make sure no background microflora, that may be misinterpreted as *E. coli* O157:H7, was being recovered on MSA supplemented with nalidixic acid. No bacterial growth was observed on any of the uninoculated control MSA plates.

Analysis of Variance (ANOVA) on the data for interaction studies in manure and rumen fluid were performed as a Randomized Complete Block Design (RCBD) using single factor Repeated Measures Analysis of Statistical Analysis System software (SAS Institute Inc., Cary, N.C.). The means of duplicate plate counts were converted to a $log_{10}$ CFU/ml scale before analysis. The treatment design was a 20×3 factorial with each plate count as a sampling unit and duplicate plate counts as an experimental unit. Differences among treatment means were determined using LSD (Least Square Difference) method.

Based on the results from interaction studies in manure and rumen fluid, bile tolerance, storage stability and identification profiles, the strains that were finally selected to be used as CEP were, M35 (ATCC accession no. PTA-5249) and L411. These two strains were selected for the following reasons: both showed significant inhibition towards *E. coli* O157:H7 in laboratory media (6.1 and 2.0 mm inhibition zones for M35 (ATCC accession no. PTA-5249) and L411 respectively), manure and rumen fluid (completely eliminated *E. coli* at 48 h); both showed increased growth under all bile conditions at all incubation periods; the API system revealed good identification for both isolates; and antibiotic susceptibility tests showed that M35 (ATCC accession no. PTA-5249) was susceptible to all the antibiotics to which it was tested, while L411 was susceptible to 4 of the 6 antibiotics tested. Although strain L411 was resistant to two antibiotics (TS and GP), the reason for its selection over other strains is that the rest of the strains did not meet more than one selection criteria when compared to L411. The selection process is summarized in Table 8.

TABLE 6

Growth of *E. coli* O157:H7 ($log_{10}$ CFU/ml) in association with cattle isolates in manure at 0, 24 and 48 hours

| Sample | API | 0 h | 24 h | 48 h |
|---|---|---|---|---|
| IC | — | 5.9 | 7.6 | 6.6 |
| C315 | *P. acidilactici* | 5.9 | 6.5 | 4.9 |
| A46 | *L. acidophilus* | 5.9 | 5.9 | 5.2 |
| C314 | *L. acidophilus* | 5.9 | 5.8 | 4.9 |
| M35 | *L. acidophilus* | 6.1 | 5.6 | 4.8 |
| M38 | *L. acidophilus* | 6.0 | 6.4 | 5.5 |
| S310 | *L. acidophilus* | 5.8 | 5.9 | 5.9 |
| B41 | *L. fermentum* | 6.0 | 6.5 | 5.7 |
| R44 | *L. acidophilus* | 6.2 | 6.3 | 5.8 |

TABLE 6-continued

Growth of *E. coli* O157:H7 (log₁₀ CFU/ml) in association with cattle isolates in manure at 0, 24 and 48 hours

| Sample | API | 0 h | 24 h | 48 h |
|---|---|---|---|---|
| I212 | *L. salivarius* | 5.8 | 5.9 | 4.9 |
| O37 | *L. cellobiosus* | 5.9 | 6.5 | 5.4 |
| L411 | *L. acidophilus* | 6.2 | 6.0 | 5.8 |
| A43 | *L. acidophilus* | 6.1 | 5.9 | 5.5 |
| H27 | *L. delb. delb.* | 6.1 | 5.9 | 5.5 |
| P31 | *L. acidophilus* | 6.3 | 5.7 | 5.4 |
| C312 | *L. acidophilus* | 6.1 | 5.4 | 4.6 |
| T21 | *Leuconostoc sp.* | 6.2 | 6.0 | 5.6 |
| T28 | *L. acidophilus* | 6.0 | 5.4 | 5.1 |
| I33 | *L. brevis* | 6.1 | 5.6 | 4.8 |
| P32 | *L. brevis* | 6.2 | 5.8 | 5.0 |

IC = Inoculated control

TABLE 7

Growth of *E. coli* O157:H7 (log₁₀ CFU/ml) in association with cattle isolates in rumen fluid at 0, 24 and 48 hours

| Sample | API | 0 h | 24 h | 48 h |
|---|---|---|---|---|
| IC | — | 5.6 | 7.1 | 7.4 |
| C315 | *P. acidilactici* | 5.6 | 5.9 | 6.0 |
| A46 | *L. acidophilus* | 5.5 | 4.9 | 1.0 |
| C314 | *L. acidophilus* | 5.6 | 4.9 | 1.0 |
| M35 | *L. acidophilus* | 5.6 | 1.0 | 1.0 |
| M38 | *L. acidophilus* | 5.7 | 4.9 | 1.0 |
| S310 | *L. acidophilus* | 5.7 | 5.9 | 2.1 |
| B41 | *L. fermentum* | 5.6 | 6.1 | 6.3 |
| R44 | *L. acidophilus* | 5.6 | 4.9 | 1.0 |
| I212 | *L. salivarius* | 5.6 | 6.1 | 6.9 |
| O37 | *L. cellobiosus* | 5.7 | 5.9 | 6.1 |
| L411 | *L. acidophilus* | 5.7 | 4.8 | 1.0 |
| A43 | *L. acidophilus* | 5.3 | 1.5 | 1.0 |
| H27 | *L. delb. delb.* | 5.5 | 3.0 | 1.0 |
| P31 | *L. acidophilus* | 5.6 | 5.9 | 5.8 |
| C312 | *L. acidophilus* | 6.3 | 5.7 | 5.6 |
| T21 | *Leuconostoc sp.* | 5.6 | 5.7 | 5.7 |
| T28 | *L. acidophilus* | 5.6 | 5.3 | 5.7 |
| I33 | *L. brevis* | 5.6 | 6.0 | 5.9 |
| P32 | *L. brevis* | 5.6 | 5.9 | 6.1 |

IC = Inoculated control

TABLE 8

Selection of isolates for competitive exclusion product

| Isolate Stability | Interaction | | Antibiotic Resistance$^\alpha$ | Storage |
|---|---|---|---|---|
| | Manure | Rumen | | |
| H27 | − | + | 4 | + |
| I212 | + | − | 0 | + |
| T21 | − | + | 4 | + |
| T28 | − | + | 1 | + |
| C312 | + | − | 0 | + |
| C314 | + | + | 5 | + |
| C315 | + | − | 2 | + |
| I33 | − | + | 1 | + |
| M35 | + | + | 0 | + |
| M38 | − | + | 2 | + |
| O37 | − | − | 2 | + |
| P31 | − | + | 2 | + |
| P32 | − | − | 2 | + |
| S310 | − | + | 2 | + |
| A43 | − | + | 0 | − |
| A46 | + | + | 2 | − |
| B41 | − | − | 3 | + |
| L411 | + | + | 2 | + |
| R44 | − | + | 2 | + |

M35 corresponds to ATCC accession no. PTA-5249

$^\alpha$Total number of antibiotics that an isolate was resistant to, out of the six antibiotics that the isolates were tested for.
+ indicates a positive result for each particular selection criteria.
− indicates a negative result for each particular selection criteria.

Example 8

Identification of Strains of Ribotyping and 16S Sequence Analysis

The genotypic fingerprint analysis of 13 isolates, used in manure and rumen fluid interaction studies, was carried out by ribotyping where total DNA of an organism, after isolation, is restricted into multiple fragments (<1 kb to >20 kb) using restriction enzyme. The restricted fragments after separation are subsequently hybridized with a probe targeted to the 16S, 23S or 5S ribosomal RNA (rRNA) genes. Restriction bands containing copies of the rRNA genes are then visualized and a characteristic fingerprint is obtained based on the pattern of the band sizes. To obtain ribotyping patterns, isolates were sent to the Laboratory for Molecular Typing at Cornell University (Ithaca, N.Y.) as MRS agar slant cultures.

The isolates selected after screening for inhibition towards *E. coli* O157:H7 in manure and rumen fluid were also identified by 16S rRNA sequence analysis. In this analysis a portion of the 16S rRNA gene of the bacteria was amplified and sequenced, and then was compared to sequences contained in the public database, Genbank, to provide matches to the isolate. Samples of selected isolates were sent as MRS agar slant cultures to the Laboratory for Molecular Typing at the Cornell University (Ithaca, N.Y.).

The genotypic identification of the selected cattle isolates was done using ribotyping. Isolates H27 and C314 were reported to be similar, with C314 having 95% homology with H27. Both isolates were identified as *L. acidophilus* showing 51-60% homology with the Dupont database patterns. Isolate R44 showed 58-78% homology with *L. acidophilus* and 58% homology with *L. amylovorus* when compared with the Dupont database. The remaining isolates did not have a close match with any of the patterns in either the Dupont or LMT database. However, isolates C312 and T28 were found closely related to each other, sharing many similar bands, with T28 showing 91% homology with C312. Isolates M35 (ATCC accession no. PTA-5249), T21, L411, A46, A43, I33, M38 and O37 also aligned closely together (homology ranging from 94%-97%). Results are shown in Tables 9, 10, and 11.

TABLE 9

Ribotyping analysis of cattle isolates as compared to the DuPont database

| LAB Strain Code | DuPont Accession No. | Significant Alignments | % Homology |
|---|---|---|---|
| H27 | DUP5000 | L. acidophilus | 60% |
|  | DUP5001 | L. acidophilus | 52% |
|  | DUP5002 | L. acidophilus | 51% |
| R44 | DUP5000 | L. acidophilus | 58% |
|  | DUP5001 | L. acidophilus | 78% |
|  | DUP5002 | L. acidophilus | 58% |
|  | DUP5005 | L. amylovorus | 58% |

TABLE 10

Ribotyping analysis of cattle isolates as compared to each other

| LAB Strain Code | Close Alignment to | % Homology |
|---|---|---|
| H27 | C314 | 95% |
| C312 | T28 | 91% |
| T21 | A46 | 97% |
|  | A43 | 97% |
|  | O37 | 97% |
|  | I33 | 96% |
|  | M35 | 96% |
|  | L411 | 95% |
|  | M38 | 94% |

Since M35 (ATCC accession no. PTA-5249) and L411 were closely aligned together in the ribotyping patterns obtained, only isolate M35 (ATCC accession no. PTA-5249) was further identified using 16S rRNA sequence analysis. Isolate M35 (ATCC accession no. PTA-5249), which was identified as *L. acidophilus* by the API fermentation pattern, gave different results with the 16S rRNA analysis. Comparison of the 16S rRNA sequence of the strain with the public database, GenBank, revealed that M35 (ATCC accession no. PTA-5249) had significant homology to *L. crispatus* (98%) (Table 11). In view of the close alignment of the isolates M35 (ATCC accession no. PTA-5249) and L411 with each other in the ribotyping analysis L411 is also speculated to be *L. crispatus*.

TABLE 11

16S rRNA sequence analysis of M35 (ATCC accession no. PTA-5249) as compared to GenBank Database. Table shows the top five matches to GenBank

| LAB Strain Code | Genbank Accession No. | Significant Alignments | % Homology (No. of |
|---|---|---|---|
| M35 | AF257097 | L. crispatus | 98% (634/644) |
|  | AF277096 | L. crispatus | 98% (634/644) |
|  | Y17362 | L. crispatus | 98% (634/644) |
|  | AF243152 | L. crispatus | 98% (634/644) |
|  | AF243158 | L. crispatus | 98% (631/643) |

Example 9

Test for Acid Tolerance and Antibiotic Resistance in LAB Selected for CEP (1) Acid Tolerance The isolates that were finally selected as CEP at the end of all the screening procedures were further tested for acid tolerance using the procedure described by Chou, L. and B. Weimer in Isolation and characterization of acid-and bile-tolerant isolates from strains of *Lactobacillus acidophilus*. J. Dairy Sci. 82: 23-31, 1999, with some modifications. An overnight culture of each strain of selected LAB was prepared by growing the frozen concentrated culture in MRS broth for 18-24 hours at 37° C. About 1 ml of the overnight culture was inoculated into 100 ml of MRS broth and incubated further at 37° C. for 18-24 hours. The cells were harvested by centrifugation at 10,000×g for 10 minutes at 0-4° C. The pellets were washed once in sterile PBS and resuspended in 100 ml of PBS to obtain a population of $1 \times 10^9$ CFU/ml. Bacterial numbers were determined by plating the cell suspension on MRS agar, using appropriate dilutions, and incubating at 37° C. for 18-24 hours. About 1% of the cell suspension was added to a series of tubes containing 10 ml MRS broth (to obtain a population of $1 \times 10^7$ CFU/ml) acidified with 2M HCl to pH 2, 4, 5, and 7 (nonacidified/control) and incubated in a water bath at 37° C. The growth of the organisms for each pH value was determined at 0, 2, 4 and 24 hours by plating on MRS agar and incubating at 37° C. The test was repeated three times for each isolate.

(2) Antibiotic Resistance

The isolates chosen for CEP at the end of the screening procedures were also tested for susceptibility to vancomycin, cephalosporin (cephalothin), and polymixin B belonging to Category I, II, and III respectively. Agar disc diffusion test (BBL Sensi-Disc Antimicrobial Susceptibility Test Discs, Benton Dickinson Microbiology Systems, Cockeysville, Md.) was used for susceptibility testing. An overnight culture of each isolate, grown on MRS agar at 37° C. for 18-24 hours, was used to make a direct suspension in 5 ml PBS with turbidity equivalent to the 0.5 McFarland turbidity standard. The cell suspension was streaked on the entire surface of a Mueller Hinton Agar plate using a sterile swab dipped into the properly adjusted inoculum. Appropriate discs containing the antibiotic were applied to the agar and incubated at 37° C. for 16-18 hours. After incubation, plates were examined for inhibition zones around the discs. Recorded zone diameters (mm) were compared to the Zone Diameter Interpretive Chart provided with the test kit, to examine the antibiotic susceptibility of the organisms. The isolates were considered susceptible to vancomycin, cephalosporin, or polymixin B if a zone diameter of greater than 15 mm, 18 mm, or 12 mm respectively, was observed around the disc. The entire test was replicated three times.

Both isolates, M35 (ATCC accession no. PTA-5249) and L411, showed increased growth at pH 4.0, 5.0, and 7.0 over a period of 24 hours as determined by the plate counts. Isolate M35 (ATCC accession no. PTA-5249) showed an increase in growth (0 to 24 h) by approximately 1.0 $\log_{10}$ cycle (7.2 to 8.3 $\log_{10}$ CFU/ml) at pH 4.0, and 2.0 $\log_{10}$ cycles (6.9 to 9.2 $\log_{10}$ CFU/ml) at pH 5.0 and 7.0. Isolate L411 showed increased growth by approximately 2.0 $\log_{10}$ cycles at pH 4.0, 5.0, 7.0. Both isolates failed to survive at pH 2.09 as no growth was observed at 2, 4, or 24 hours. Results shown in Table 12.

The antibiotic susceptibility test of M35 (ATCC accession no. PTA-5249) and L411 towards vancomycin, cephalosporin, and polymixin B revealed that both isolates were susceptible to the three antibiotics. Both the isolates exhibited zones greater than 15 mm, 18 mm, and 12 mm for vancomycin and cephalosporin respectively.

TABLE 12

Acid tolerance of M35 (ATCC accession no. PTA-5249) and L411 based on their growth ($\log_{10}$ CFU/ml) at pH 2.0, 4.0, 5.0 and 7.0 at 0, 2, 4, and 24 h

| Isolate | Time Period | pH 2.0 | pH 4.0 | pH 5.0 | pH 7.0 |
|---------|-------------|--------|--------|--------|--------|
| M35     | 0 h         | 6.9    | 7.2    | 6.9    | 6.9    |
|         | 2 h         | 1.0    | 7.2    | 7.3    | 7.0    |
|         | 4 h         | 1.0    | 7.6    | 8.5    | 7.8    |
|         | 24 h        | 1.0    | 8.3    | 9.2    | 9.2    |
| L411    | 0 h         | 6.8    | 6.8    | 7.2    | 7.1    |
|         | 2 h         | 1.0    | 7.2    | 8.0    | 7.3    |
|         | 4 h         | 1.0    | 7.4    | 8.1    | 7.7    |
|         | 24 h        | 1.0    | 8.6    | 9.0    | 9.0    |

Example 10

Preparation of Frozen Concentrated Cultures (FCC) of Selected LAB

The strains finally selected as CEP cultures were grown separately into 200 ml MRS broth at 37° C. for 24 hours. Cells were harvested by centrifugation at 10,000×g for 10 minutes at 0° C. and pellets resuspended in 20 ml of 10% non-fat milk solids (NFMS). About 2 ml of each culture suspension was transferred to 2 ml vials and immediately transferred to liquid nitrogen. After freezing in liquid nitrogen, the vials containing the FCC were stored at −70° C.

Example 11

Antagonistic Effect of Developed and Commercial CEP on *E. coli* O157:H7 in Manure and Rumen Fluid M35 (ATCC accession no. PTA-5249) was further tested for its antagonism towards *E. coli* O157:H7 in manure and rumen fluid along with a mixture of commercial strains of CE microorganisms (*L. acidophilus* LA45, and *L. acidophilus* LA51) obtained from Nutrition Physiology Corporation (NPC) (Indianapolis, Ind.). A mixture of commercial strains (NPC) was prepared by combining together 1 ml of a 1:10 dilution (1 ml FCC into 9 ml of sterile 10% NFMS) of each commercial strain. The UNL mixture was prepared by combining together 1 ml of FCC of each selected LAB (M35 (ATCC accession no. PTA-5249) and L411). One of the selected UNL strains (M35 (ATCC accession no. PTA-5249)) was also combined with one of the commercial strains (LA51) (1:1) and the mixture (UNL+NPC) tested for inhibition towards *E. coli* O157:H7 in manure and rumen fluid.

Manure and rumen fluid samples of cattle were obtained from Animal Science Dept., UNL, and rumen fluid treated the same way as previously described. Keeping aside 10 g of manure or rumen sample as uninoculated control, about 40 g of the sample was inoculated with 0.04 ml of four-strain-cocktail of nalidixic acid-resistant *E. coli* O157:H7. The inoculated sample was divided into portions of 10 g each. Reserving one portion as inoculated control, each of the other portions was inoculated with 1 ml of UNL, NPC, or UNL+NPC mixture. All samples were incubated at 37° C. and *E. coli* growth was monitored at 0, 24, and 48 hours by plating on MSA supplemented with nalidixic acid (50 μg/ml). Incubation for tests in rumen fluid was carried out under anaerobic conditions. The tests in manure and rumen fluid were replicated three times.

Figure 5:
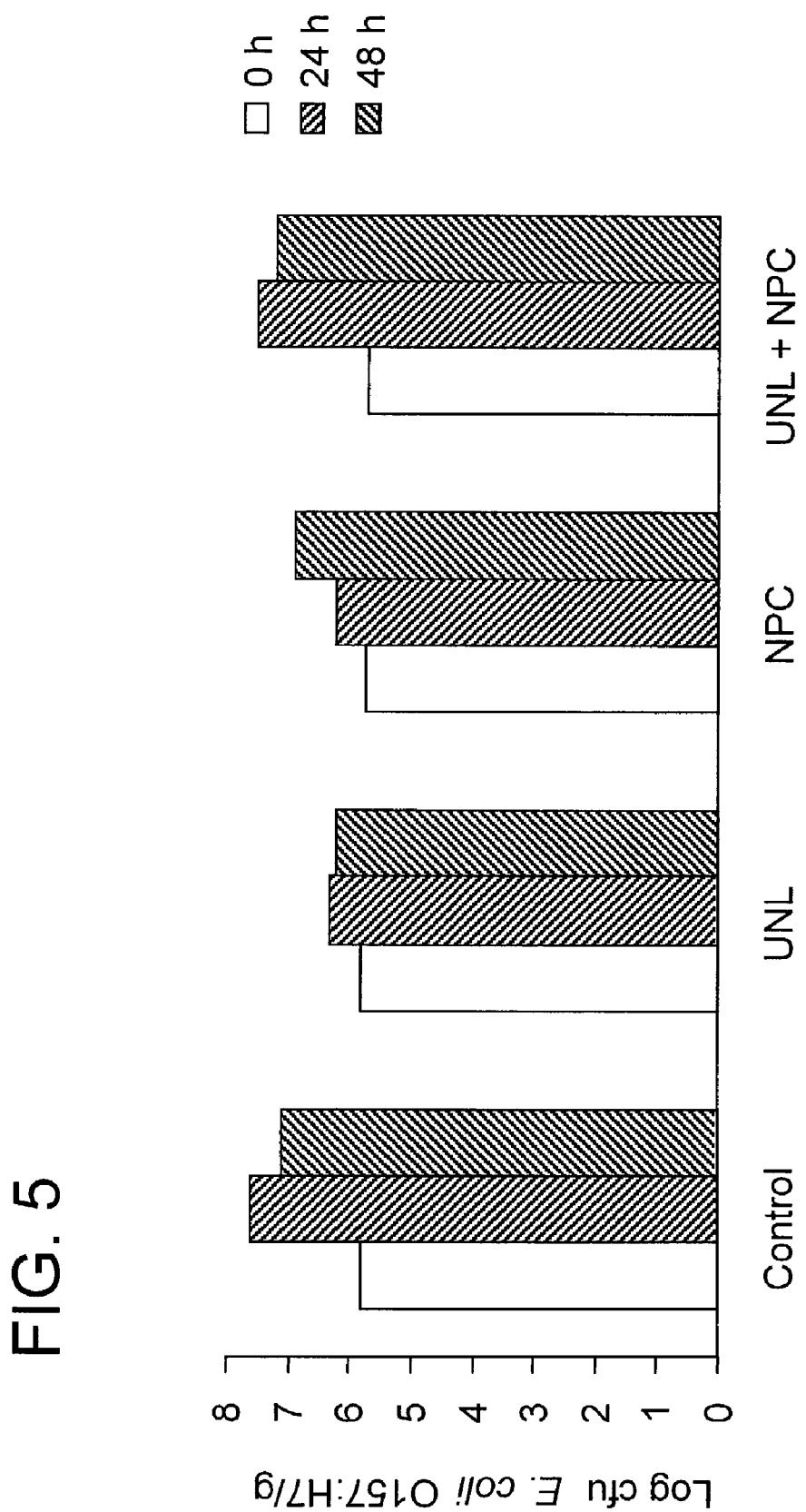
FIG. 5 is a graphic representation of inhibition of *E. coli* O157:H7 by competitive exclusion product (CEP) in manure. UNL represents a mixture of isolates M35 (ATCC accession no. PTA-5249) and LA45. NPC represents a mixture of commercial strains LA51 and LA45. The control sample contained only the *E. coli* O157:H7 strain.
Figure 6:
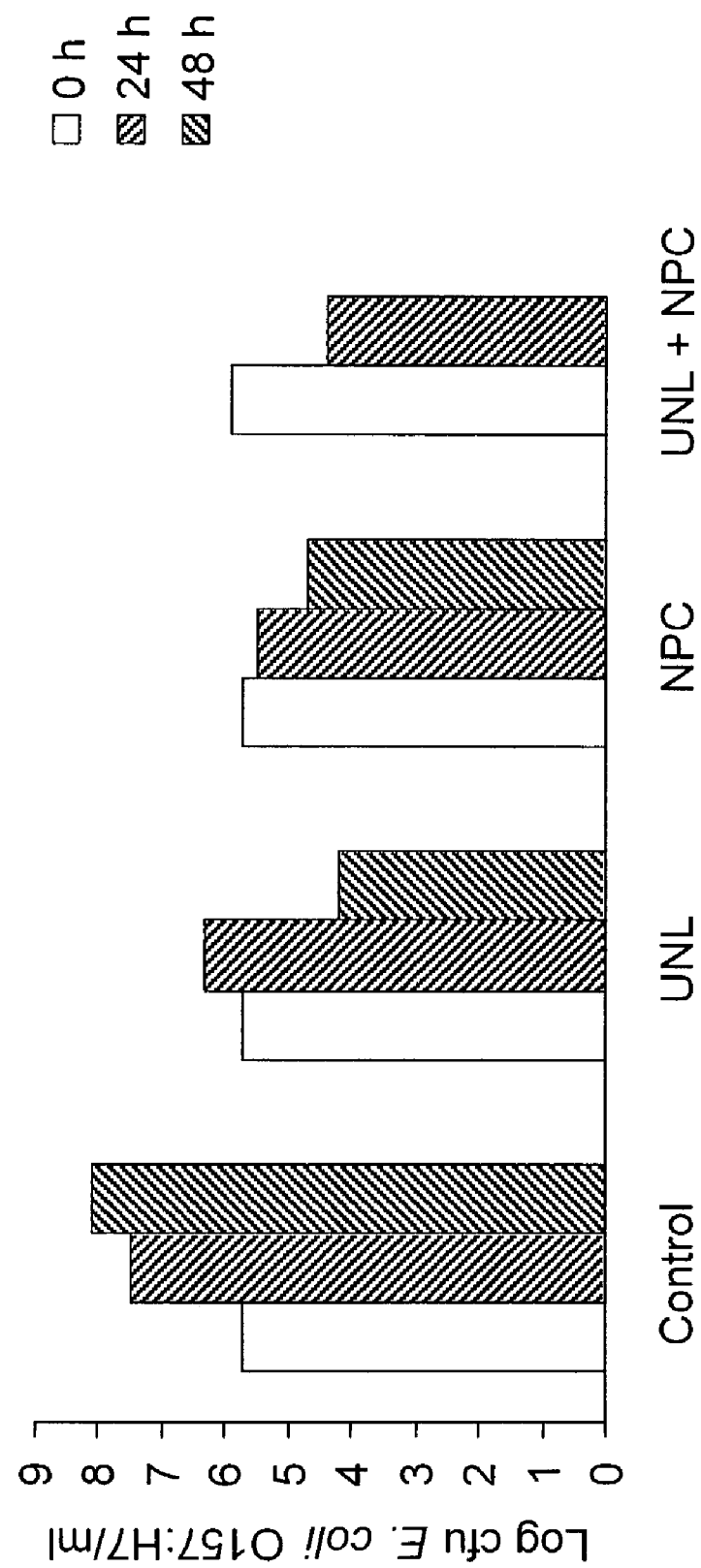
FIG. 6 is a graphic representation of inhibition of *E. coli* O157:H7 by competitive exclusion product (CEP) in rumen fluid. UNL represents a mixture of isolates M35 (ATCC accession no. PTA-5249) and LA45. NPC represents a mixture of commercial strains LA51 and LA45. The control sample contained only the *E. coli* O157:H7 strain.

The mixtures of developed CEP (M35 (ATCC accession no. PTA-5249)) and strains from a commercial CEP were further tested for inhibition against *E. coli* O157:H7 in manure and rumen fluid. None of the CEP mixtures (UNL, NPC, and UNL+NPS) showed a reduction in *E. coli* counts in manure over a period of 48 hours when compared to control. However, in rumen fluid, UNL+NPC reduced *E. coli* counts considerably at 24 hours (~2 $\log_{10}$ cycles) and eliminated *E. coli* completely at 48 hours (reduction from 5.5 $\log_{10}$ CFU/ml to 1.0 $\log_{10}$ CFU/ml), whereas UNL and NPC showed a reduction in *E. coli* counts only at 48 hours and not 24 hours. Results shown in Table 13 and FIGS. 5 and 6.

TABLE 13

Growth of *E. coli* O157:H7 ($\log_{10}$ CFU/ml) in association with competitive exclusion products in manure and rumen fluid

| Treatment | E. coli counts in Manure | | | E. coli counts in Rumen Fluid | | |
|-----------|------|------|------|------|------|------|
| Fluid     | 0 h  | 24 h | 48 h | 0 h  | 24 h | 48 h |
| IC        | 5.8  | 7.5  | 7.1  | 5.7  | 7.5  | 8.1  |
| UNL       | 5.7  | 6.3  | 6.2  | 5.7  | 6.3  | 4.2  |
| NPC       | 5.7  | 6.0  | 6.9  | 5.7  | 5.5  | 4.7  |
| UNL + NPC | 5.7  | 7.5  | 7.0  | 5.9  | 4.4  | 1.0  |

IC - Inoculated Control; UNL - Mixture of isolates M35 (ATCC accession no. PTA-5249) and L411; NPC - Mixture of commercial strains LA51 and LA45.

Example 12

Test for Interaction Among LAB

The final strains selected as CEP (M35 (ATCC accession no. PTA-5249) and L411) and the commercial strain (LA51) used in the interaction studies above were further tested for inhibition against each other using the agar spot test. An overnight culture of M35 (ATCC accession no. PTA-5249), L411 or LA51 in MRS broth was spot-induced on MRS agar plate and incubated for 24 hours at 37° C. in plastic bags flushed with $CO_2$ for 30 seconds. About 1 ml of an overnight culture of each strain was inoculated individually into 10 ml of tempered MRS agar (Difco) to obtain a final concentration of approximately $5 \times 10^7$ CFU/ml. This mixture was then poured onto the surface of spot-inoculated agar plates that contained well-grown colonies of test bacteria. After 24 hours of incubation at 37° C. inhibitory activity was measured as the size of inhibition zones around the colony. Inhibition was considered positive if the width of the clear zone around the colonies was ≧0.5 mm. The test was repeated three times.

The LAB used in CE mixtures were also tested for antagonism against each other using the agar spot test. As the results indicated (Table 14), both isolates, M35 (ATCC accession no. PTA-5249) and L411, were being inhibited by LA51, while isolates M35 (ATCC accession no. PTA-5249) and L411 were inhibiting each other. However, neither of the two cattle isolates (M35 (ATCC accession no. PTA-5249) and L411) showed any antagonistic effect against LA51.

TABLE 14

Inhibition of lactic acid
bacteria (M35 (ATCC accession no. PTA-5249), L411, and
LA51) towards each other using agar spot test
Inhibiting Isolates

| | Zone of Inhibition (mm) | | |
|---|---|---|---|
| Test Isolates | LA51 | L411 | M35 |
| M35 | 1.40 | 0.99 | — |
| L411 | 1.27 | — | 1.27 |
| LA51 | — | 0.00 | 0.00 |

Example 13

Live Animal Studies

Cattle. One hundred eighty-five (185) steers of British breeding (primarily Angus, Hereford, and Angus x Hereford) were purchased through Caprock Industries, Inc. and transported to the Texas Tech University Burnett Center. Following arrival, the cattle were unloaded and processed. Processing included: 1) individual body weight (BW) measurement; 2) uniquely numbered ear tag in the left ear; 3) vaccination with UltraChoice 7 (Pfizer Animal Health; Lot No. S900024 Exp. Jul. 5, 2001 and Lot No. S903222B Exp. Sep. 10, 2001); 4) vaccination with Bovishield 4+Lepto (Pfizer Animal Health; Ser. No. SNA019266/A013371 Exp Oct. 1, 2002; Ser. No. SNA018354/A019248 Exp. Sep. 11, 2002); and 5) treatment down the back line with Dectomax (Pfizer Animal Health; Lot No. K9T04911 Exp. July, 2002). Steers were sorted to 37 concrete, partially slotted floor pens with five steers per pen and offered 10 lb/steer of a 65% concentrate starter diet. On Jun. 6, 2001 all cattle switched to a 70% concentrate diet, and the switch to an 80% concentrate diet occurred on Jun. 11, 2001.

All cattle were weighed on Jun. 12, 2001 to initiate the preliminary phase of the experiment. At this time, each steer was implanted with Revalor S (Intervet; Lot No. 321 Exp. November, 2002) in the right ear. Pen assignments were retained from the original sort that had occurred at the time of arrival processing. On Jun. 16, 2001 all cattle were switched to the final 90% concentrate diet (Table 1). Each steer was weighed on Jul. 31, 2001 (49 d on feed), and an individual fecal sample was obtained to test for shedding of E. coli 0157:H7.

Treatment and Pen Assignments. Five steers (one with injured foot, one with an injured shoulder, one that did not gain BW for the first 49 d, and the two steers of lightest BW among the remaining cattle) were designated as extra cattle, leaving 180 steers for the experiment.

Each steer was weighed on Aug. 14, 2001 to begin the study. Treatments (control and the two Lactobacillus acidophilus cultures) were applied when the cattle were fed after they were returned to their pens.

The experimental design was a randomized complete block, with pen as the experimental unit (12 pens per each of the three treatments with five steers per pen for a total of 180 steers). The three treatments were as follows:

Control standard TTU Burnett Center 90% concentrate diet with carrier (lactose) only mixed in water and added to the diet at the time of feeding;

NP 747 standard TTU Burnett Center 90% concentrate diet with 1×10$^9$ CFU Lactobacillus acidophilus Strain NPC 747 (provided by University of Oklahoma) mixed in water and added to the diet at the time of feeding;

NP 750 standard TTU Burnett Center 90% concentrate diet with 1×10$^9$ CFU Lactobacillus acidophilus Strain NPC 750 (isolate M35 (ATCC accession no. PTA-5249)) mixed in water and added to the diet at the time of feeding.

Each treatment culture (lactose for the control treatment) was prepackaged in aluminum foil packets by personnel of Nutrition Physiology Corp., Indianapolis, Ind. The contents of one packet were sufficient to supply the desired dose of microbial culture for the 12 pens of cattle on each treatment. The contents of the packet for each treatment were mixed with 2.5 L of distilled water in a plastic sprinkler can, after which the contents of the sprinkler can were poured onto the diet as it mixed in a Rotomix 84-8 mixer/delivery unit.

Experimental Diets. Ingredient composition of the 90% concentrate diet fed during the experiment is shown in Table 15. These data reflect adjustments for the average dry matter (DM) matter content of feed ingredients for the period during which microbial culture treatments were applied. Each diet contained the same intermediate premix (Table 15), which supplied protein, various minerals and vitamins, Rumensin (30 g/ton, DM basis), and Tylan (8 g/ton, DM basis).

TABLE 15

Ingredient composition (%, DM basis)
of the 90% concentrate experimental diet

| Ingredient | Percentage of DM |
|---|---|
| Alfalfa hay, ground | 4.96 |
| Cottonseed hulls | 5.04 |
| Steam-flaked corn | 64.60 |
| Dry-rolled corn | 10.15 |
| Cottonseed meal | 4.82 |
| Molasses | 4.12 |
| Fat (yellow grease) | 2.93 |
| Urea | 0.90 |
| Premix[a] | 2.48 |

[a]Composition of the premix was as follows: cottonseed meal = 23.9733; high-calcium limestone = 42.1053; dicalcium phosphate = 1.0363; potassium chloride = 8.000; magnesium oxide = 3.5587; ammonium sulfate = 6.6667; salt = 12.000; cobalt carbonate = 0.0017; copper sulfate = 0.1572; iron sulfate = 0.1333; EDDI = 0.0025; manganese oxide = −0.2667; selenium premix, .2% Se = 0.1000; zinc sulfate = 0.8251; vitamin A, 650,000 IU/g = 0.0122; vitamin E, 275 IU/g = 0.1260; Rumensin, 80 mg/lb = 0.6750; and Tylan, 40 mg/lb = 0.3600. Concentrations by the certain ingredients are on a 90% DM basis.

Procedures and Data Collection. Standard procedures at the Burnett Center were used throughout the experiment. The three treatment diets were mixed in a 45-cubic foot capacity Marion paddle mixer. The Burnett Center feed milling system is operated by a computer-controlled batching system. A printout of the weight of each dietary ingredient was recorded on a daily ingredient usage output from the computerized batching system. Once the total amount of feed for a given treatment was mixed, the mixed batch was released from the Marion paddle mixer and delivered by a drag-chain conveyer to a Rotomix 84-8 delivery system. After feed was delivered, and the mixer unit for the Rotomix 84-8 unit was operating, the contents of the sprinkler can for a given treatment were poured onto the diet. After mixing for approximately 4 to 5 min, the quantity of feed allotted to each of the 12 pens within treatment was then weighed to the nearest 1 lb by use of the load cells and indicator on the Rotomix 84-8 unit. Feeding order of treatment diets throughout the experiment was Control, NPC 747, and NPC 750. Clean-out of the Rotomix 84-8 was monitored closely to avoid cross-contamination of diets, and at least one batch of a diet from another experiment (equivalent to the Control diet) was mixed between the NPC 747 and NPC 750 treatment diets.

Dry matter determinations on ingredients used in the experimental diets were made every 2 wk throughout the experiment. These ingredient DM values were used to calculate the DM percentage of each dietary ingredient during the experiment. In addition, samples of mixed feed delivered to feed bunks were taken weekly throughout the experiment. These bunk sample DM values were used to compute average DM intake (DMI) by the cattle in each pen. Samples of feed taken from the bunk were composited for the entire preliminary period and for each interval in which cattle were weighed (typically 28-d intervals) after the microbial culture treatments were initiated. Composited feed samples were ground to pass a 2-mm screen in a Wiley mill and analyzed for DM, ash, crude protein (CP), acid detergent fiber (ADF), Ca, and P (AOAC, 1990).

Each feed bunk of the 36 pens was evaluated daily. The quantity of feed remaining in each bunk was estimated, and the suggested daily allotment of feed for each pen was recorded. This bunk-reading process was designed to allow for little or no accumulation of unconsumed feed (0 to 1 lb per pen). A computer printout of the intake by each pen for the previous 3-d period was available each morning to assist with bunk reading. Pens of cattle that maintained a given level of feed intake for a 3-d period were challenged to consume a higher level (0.4 lb/steer challenge). Each challenge level was maintained for a 3-d period when the pen accepted the challenge and consumed all the feed offered. The ultimate goal of the challenge process was to ensure that the cattle were consuming the maximum quantity of feed possible. Feed bunks were cleaned, and unconsumed feed was weighed (Ohaus electronic scale, ±0.1 lb) at intervals corresponding to intermediate weigh dates throughout the trial. Dry matter content of these bunk weigh back samples was determined in a forced-air oven by drying overnight (typically 20 h) at 100° C. All weights for DM determinations were obtained on an Ohaus electronic balance (±0.1 g). The DMI by each pen was calculated by multiplying the DM content of the delivered feed by the total feed delivery to each pen, with correction for the DM of any feed weighed back from each pen.

Statistical Analyses. All performance data were analyzed with pen as the experimental unit. A complete randomized block design was employed, and computations were made with the GLM procedure of SAS (1987). Pen means for daily gain (ADG) and average daily DMI were included in the data file, and feed:gain ratio was computed as the quotient of daily DMI divided by ADG. The effect of treatment and block were included in the model for pen-based data.

Microbiological Measurements Monitored. Fecal samples were taken directly from the rectum of the animal initially and every 28 d thereafter until they received probiotic supplementation. Following probiotic supplementation, fecal samples were taken every 14 d. A newly developed assay for the detection of *E. coli* O157:H7 was used to detect the organism in this study (modification of Elder, R. O., J. E. Keen, G. R. Siragusa, G. A. Barkocy-Gallagher, M. Koohmarie, and W. W. Lagreid. 2000. Correlation of enterohemorrhagic *Escherichia coli* O157:H7 prevalence in feces, hides, and carcasses of beef cattle during processing. Proc. Natl. Acad. Sci. 97: 2999-3003). This method is very sensitive and will detect *E. coli* O157:H7 when numbers are very low. The method was originally developed at the Meat Animal Research Center in Clay Center, NE. Briefly, ninety milliliters of GN-VCC broth were inoculated with 10 g of feces (GN-VCC is GN broth with 8 mg/mL of vancomycin, 50 ng/mL of cefixime and 10 mg/mL of cefsulodin) and incubated for 6 h at 37° C. *E. coli* cells were subjected to immunomagnetic separation by mixing 1 mL of the culture above with 20 µl of Dynal O157 beads for 30 min at room temperature. Beads were washed three times in PBS-Tween 20 and 50 mL of the bead-bacteria mixture were spread on to CT-SMAC plates (SMAC containing 50 ng/mL of cefixime and 2.5 ug/mL of tellurite) and streaked for isolation. Plates were incubated overnight at 37° C. Three sorbitol-negative colonies were picked and streaked for isolation on CT-SMAC (to verify purity of colony selection). Plates were incubated overnight at 37° C. A single colony from the CT-SMAC plate above was selected and inoculated into MacConkey agar, Fluorocult agar, and MacConkey broth. Broth was incubated overnight at 37° C. MUG-negative, lactose-positive colonies were selected, and indole, TSI, and VP tests were conducted on selected colonies. Colonies that were indole-positive, A/A, or K/A plus gas and VP-negative were boiled (using cells from the MacConkey broth above) and tested for the O157 antigen using a Remel latex agglutination kit. Colonies were subcultured on to blood agar. The H7 agglutination and API 20 tests were conducted on O157-positive cells for confirmation.

Results. Upon arrival at the feedlot, only three of the animals had detectable amounts of the pathogen. Just before probiotic supplementation, 24 of the animals had detectable amounts of the pathogen in fecal grab samples. These animals were distributed equally among the three treatment groups.

Figure 7:
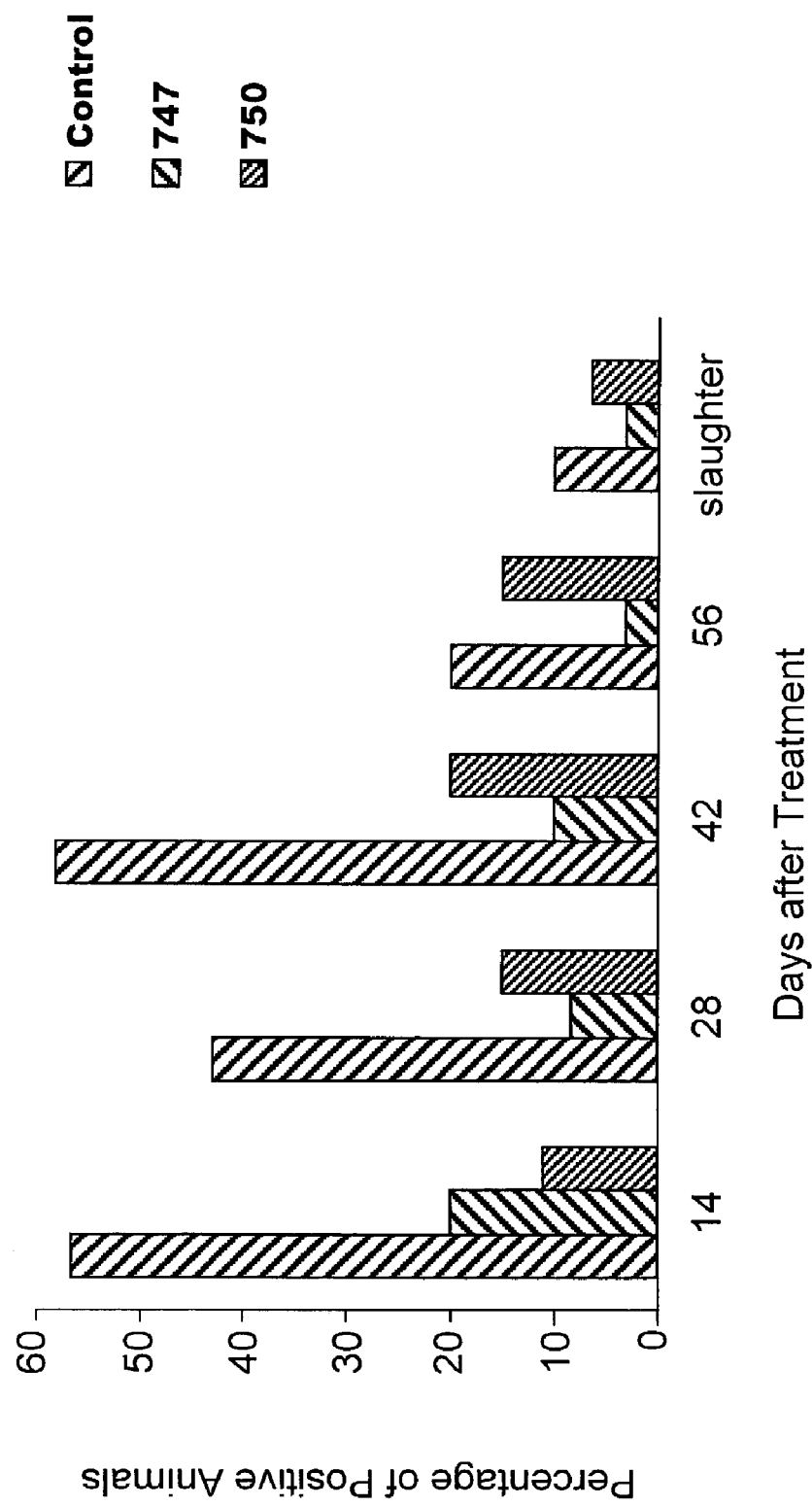
FIG. 7 is a graphic representation of incidence of *E. coli* O157:H7 in 180 cattle (60/treatment) after treatment with a competitive exclusion product (CEP). The CEPs, 747 and 750, as well as the control are described in more depth in example 13.
Figure 8:
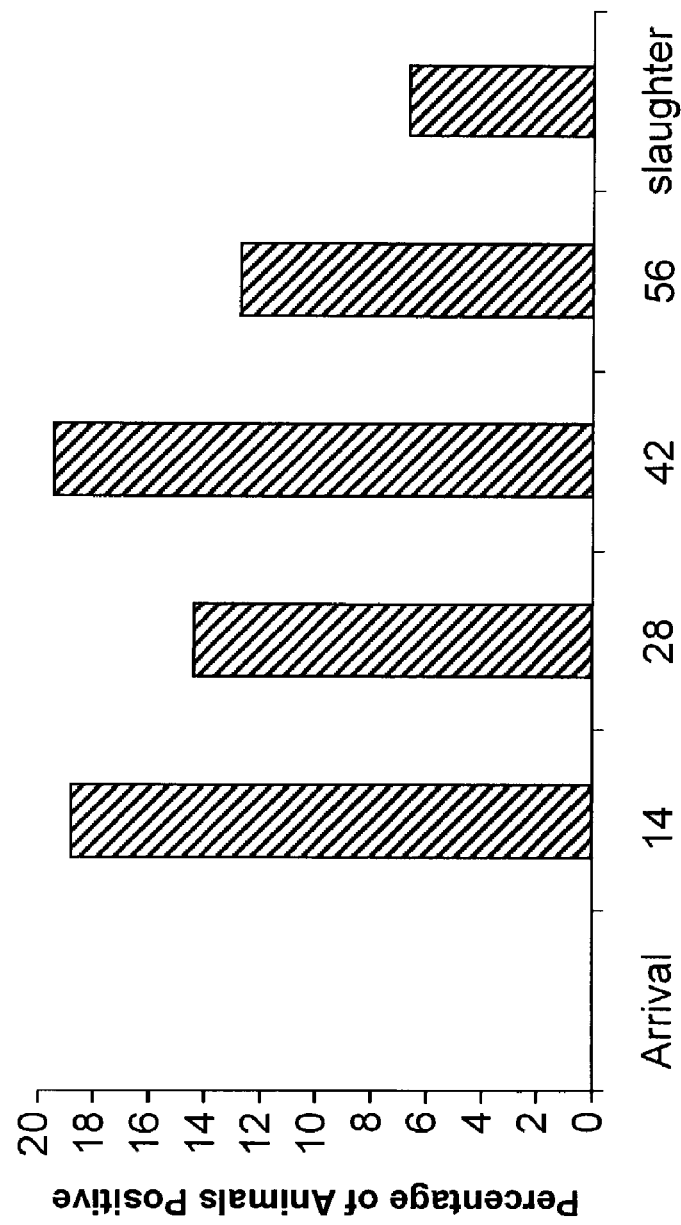
FIG. 8 is a graphic representation of incidence of *E. coli* O157:H7 in cattle that received treatment with a CEP. This figure is described in more depth in example 13.

As FIGS. 7 and 8 show, both individual animal samples and pen samples taken 14 and 28 days following the start of the treatment indicate that NPC 750 and NPC 747 significantly reduced shedding compared to the control treatment. Early in treatment (day 14) NPC 750 was more effective at reducing shedding than NPC 747. On day 42, there were significant differences for individual animal samples but not for pen data. Again, when looking at individual samples, shedding was reduced in NPC treatment groups compared to the control group.

Analyzed nutrient content of the 90% concentrate diet fed during the treatment period was generally in close agreement with formulated values. Averaged over the treatment feeding period, the diet contained (DM basis) 12.69% CP, 4.5% ash, 8.82% ADF, 0.56% Ca, and 0.30% P.

Average daily gain (Table 16) did not differ among treatments ($P>0.10$), but cattle in both the Lactobacillus culture groups had numerically higher ADG for the first 28 d of the treatment feeding period. In addition, cattle in the NPC 747 and NPC 750 treatments tended ($P\leq0.144$) to have greater adjusted ADG (calculated from adjusted final BW) for the overall study than control cattle. Dry matter intake did not differ among treatments ($P>0.10$) for the first 28 d or for the overall treatment period. Similarly, feed:gain ratio did not differ ($P>0.10$) for the first 28 d or for the overall period; however, feed:gain ratio based on adjusted ADG tended ($P\leq0.067$) to be improved for the two probiotic culture treatments than for the control.

TABLE 16

Effects of live cultures of
Lactobacillus acidophilus Strains NPC 747
and NPC 750 on performance by finishing beef steers

| Item | Treatment | | | |
|---|---|---|---|---|
| | Control (C) | NPC 747 | NPC 750 | SE[b] |
| Initial BW, lb | 1,037.2 | 1,029.1 | 1,029.6 | 2.38 |
| Final BW, lb | 1,277.1 | 1,271.5 | 1,283.4 | 6.90 |
| Adjusted final BW, lb[c] | 1,272.1 | 1,276.4 | 1,283.4 | 7.69 |
| Daily gain, lb | | | | |
| d 0 to 28 | 4.07 | 4.28 | 4.33 | 0.150 |
| d 0 to end | 3.50 | 3.49 | 3.65 | 0.101 |
| Adjusted 0 to end[c] | 3.44 | 3.58 | 3.69 | 0.106 |
| Daily DMI, bl/steer | | | | |
| d 0 to 28 | 20.02 | 20.29 | 20.36 | 0.264 |
| d 0 to end | 20.54 | 20.32 | 20.85 | 0.249 |
| Feed: gain | | | | |
| d 0 to 28 | 4.94 | 4.84 | 4.73 | 0.133 |
| d 0 to end | 5.94 | 5.92 | 5.76 | 0.116 |
| Adjusted d 0 to end | 6.01 | 5.75 | 5.66 | 0.127 | control = standard T.U. Burnett Center 90% concentrate diet with carrier (lactose) only mixed in water and added to the diet at the time of feeding; NOC 747 = Control + 1 × 19$^9$ CAU Lactobacillus acidophilus Strain NPC 747 per animal; NPC 750 = Control + 1 × 10$^9$ CAU Lactobacillus acidophilus Strain NPC per animal. Average days on feed = 70.
[b]Pooled standard error of treatment means, n = 12 pens per treatment
[c]Adjusted final BW was calculated as follows: (Hot carcass weight/average dress of 62.41%). Adjusted daily gain was calculated as follows: (Adjusted final BW − initial BW)/days on feed. Adjusted feed:gain was the ratio of daily DMI and adjusted daily gain.

What is claimed is:

1. A composition comprising a biologically pure, isolated *Lactobacillus acidophilus* strain ATCC accession Number PTA-5249,
   wherein said strain inhibits *Escherichia coli* O157:H7;
   wherein said strain is resistant to from 1 to 4 antibiotics selected from the group consisting of erythromycin, tetracycline, ampicillin, grepafloxicin, levofloxacin, trimethoprim-sulfamethoxazole, vancomycin, cephalothin and polymyxin B, and
   wherein the inhibition occurs in the ruminal fluid and manure of cattle.

2. The composition of claim 1, wherein said *Escherichia coli* O157:H7 is nalidixic acid-resistant.

3. The composition of claim 1, wherein said strain is tolerant to bile.

4. The composition of claim 3, wherein the bile is oxgall.

5. The composition of claim 1, wherein said strain will remain viable when exposed to an environment maintained at 0° C.

6. The composition of claim 5, wherein said exposure is for three months.

* * * * *